United States Patent
Sookraj

(10) Patent No.: US 10,676,426 B2
(45) Date of Patent: Jun. 9, 2020

(54) ACRYLONITRILE DERIVATIVES FROM EPOXIDE AND CARBON MONOXIDE REAGENTS

(71) Applicant: Novomer, Inc., Boston, MA (US)

(72) Inventor: Sadesh H. Sookraj, Cambridge, MA (US)

(73) Assignee: Novomer, Inc., Rochester, NY (US)

( * ) Notice: Subject to any disclaimer, the term of this patent is extended or adjusted under 35 U.S.C. 154(b) by 0 days.

(21) Appl. No.: 16/023,136

(22) Filed: Jun. 29, 2018

(65) Prior Publication Data

US 2019/0002400 A1    Jan. 3, 2019

Related U.S. Application Data

(60) Provisional application No. 62/527,340, filed on Jun. 30, 2017.

(51) Int. Cl.

| | | |
|---|---|---|
| *C07C 253/26* | (2006.01) | |
| *C07C 255/08* | (2006.01) | |
| *C08L 67/04* | (2006.01) | |
| *C07D 305/12* | (2006.01) | |
| *C07C 51/347* | (2006.01) | |
| *C07C 51/09* | (2006.01) | |

(52) U.S. Cl.
CPC ............ *C07C 253/26* (2013.01); *C07C 51/09* (2013.01); *C07C 51/347* (2013.01); *C07C 255/08* (2013.01); *C07D 305/12* (2013.01); *C08L 67/04* (2013.01)

(58) Field of Classification Search
CPC .................................................. C07C 253/26
See application file for complete search history.

(56) References Cited

U.S. PATENT DOCUMENTS

| | | |
|---|---|---|
| 2,375,005 A | 5/1945 | Kung |
| 2,525,794 A | 10/1950 | Gresham et al. |
| 2,548,155 A | 4/1951 | Gresham et al. |
| 2,749,355 A | 6/1956 | Jones |
| 3,043,860 A | 7/1962 | Phillips et al. |
| 3,169,945 A | 2/1965 | Hostettler |
| 3,230,246 A | 1/1966 | Callahan |
| 3,458,561 A | 7/1969 | Kautter et al. |
| 3,678,069 A | 7/1972 | Busler |
| 3,885,155 A | 5/1975 | Anbar |
| 3,914,395 A | 10/1975 | Finelli et al. |
| 4,069,297 A | 1/1978 | Saito et al. |
| 4,178,413 A | 12/1979 | Demunda |
| 4,427,884 A | 1/1984 | Anbar |
| 4,503,001 A | 3/1985 | Grasselli |
| 4,554,024 A | 11/1985 | Zimmer et al. |
| 4,767,878 A | 8/1988 | Grasselli |
| 4,863,891 A | 9/1989 | Grasselli |
| 4,904,812 A | 2/1990 | Hoelderich et al. |
| 4,973,841 A | 11/1990 | Purser |
| 5,061,414 A | 10/1991 | Engle |
| 5,093,299 A | 3/1992 | Suresh |
| 5,310,948 A | 5/1994 | Drent |
| 5,359,081 A | 10/1994 | Drent |
| 5,438,194 A | 8/1995 | Koudijs |
| 5,648,452 A | 7/1997 | Schechtman |
| 5,661,299 A | 8/1997 | Purser |
| 5,686,027 A | 11/1997 | Olsen et al. |
| 6,133,402 A | 10/2000 | Coates |
| 6,143,915 A | 11/2000 | Zhou |
| 6,316,590 B1 | 11/2001 | Coates |
| 6,538,101 B2 | 3/2003 | Coates |
| 6,608,170 B1 | 8/2003 | Coates |
| 6,638,883 B2 | 10/2003 | Gaffney et al. |
| 6,825,865 B2 | 11/2004 | Fujimoto et al. |
| 6,852,865 B2 | 2/2005 | Coates |
| 7,420,064 B2 | 9/2008 | Luinstra |
| 8,137,810 B2 | 3/2012 | Ise et al. |

(Continued)

FOREIGN PATENT DOCUMENTS

| | | |
|---|---|---|
| WO | 2003/018540 A1 | 3/2003 |
| WO | 2010/118128 A1 | 10/2010 |

(Continued)

OTHER PUBLICATIONS

Argentina Patent Application No. 20180102556, filed on Sep. 7, 2018, titled "Acrylonitrile Compounds and Other Nitrile Compounds, and Methods of Producing and Using Thereof".

Billingham et al., "Polymerization and Copolymerizationof β-Butyrolactone by Aluminium Compounds", Journal of Organometallic Chemistry, vol. 341, No. 1-3, 1988, pp. 83-93.

Church et al., "Carbonylation of Heterocycles by Homogeneous Catalysts", Chemical Communications, vol. 21, No. 7, 2007, pp. 657-674.

Hori et al., "Ring-Opening Polymerization of Optically Active β-Butyrolactone using Distannoxane Catalysts: Synthesis of High-Molecular-Weight Poly(3-Hydroxybutyrate)", Macromolecules, vol. 26, No. 20, 1993, pp. 5533-5534.

International Search Report and Written Opinion received for PCT/Patent Application No. PCT/US2018/049890, dated Nov. 23, 2018, 13 pages.

(Continued)

*Primary Examiner* — Joseph R Kosack

(74) *Attorney, Agent, or Firm* — Young Basile Hanlon & MacFarlane, P.C.

(57) ABSTRACT

The present invention is directed to reactor systems and processes for producing acrylonitrile and acrylonitrile derivatives. In preferred embodiments of the present invention, the processes comprise the following steps: introducing an epoxide reagent and carbon monoxide reagent to at least one reaction vessel through at least one feed stream inlet; contacting the epoxide reagent and carbon monoxide reagent with a carbonylation catalyst to produce a beta-lactone intermediate; polymerizing the beta-lactone intermediate with an initiator in the presence of a metal cation to produce a polylactone product; heating the polylactone product under thermolysis conditions to produce an organic acid product; optionally esterifying the organic acid product to produce one or more ester products; and reacting the organic acid product and/or ester product with an ammonia reagent under ammoxidation conditions to produce an acrylonitrile product.

9 Claims, 5 Drawing Sheets

(56) References Cited

U.S. PATENT DOCUMENTS

| | | |
|---|---|---|
| 8,445,703 B2 | 5/2013 | Allen |
| 8,796,475 B2 | 8/2014 | Allen et al. |
| 8,845,938 B2 | 9/2014 | Ichikawa et al. |
| 9,096,510 B2 | 8/2015 | Porcelli et al. |
| 9,156,803 B2 | 10/2015 | Allen et al. |
| 9,206,144 B2 | 12/2015 | Allen et al. |
| 9,212,236 B2 | 12/2015 | Cho et al. |
| 9,327,280 B2 | 5/2016 | Lee et al. |
| 9,403,788 B2 | 8/2016 | Lee et al. |
| 9,493,391 B2 | 11/2016 | Allen et al. |
| 9,683,314 B2 | 6/2017 | Xu et al. |
| 9,719,037 B2 | 8/2017 | Sookraj |
| 9,738,784 B2 | 8/2017 | Allen et al. |
| 9,914,689 B2 | 3/2018 | Porcelli et al. |
| 10,065,914 B1 | 9/2018 | Ruhl et al. |
| 10,099,988 B2 | 10/2018 | Farmer et al. |
| 10,099,989 B2 | 10/2018 | Sookraj |
| 10,144,802 B2 | 12/2018 | Sookraj |
| 10,221,150 B2 | 3/2019 | Farmer et al. |
| 10,221,278 B2 | 3/2019 | Lee et al. |
| 10,245,559 B2 | 4/2019 | Lapointe et al. |
| 2005/0014977 A1 | 1/2005 | Drent et al. |
| 2007/0161806 A1 | 7/2007 | Preishuber-Pflugl et al. |
| 2012/0123137 A1 | 5/2012 | Allen et al. |
| 2013/0165670 A1 | 6/2013 | Allen et al. |
| 2013/0209775 A1 | 8/2013 | Allen et al. |
| 2013/0281715 A1 | 10/2013 | Allen et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0141693 A1 | 5/2015 | Allen et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0288057 A1 | 10/2016 | Lapointe et al. |
| 2017/0002136 A1 | 1/2017 | Sookraj |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0153746 A1 | 6/2018 | Sookraj |
| 2018/0155490 A1 | 6/2018 | Sookraj |
| 2018/0155491 A1 | 6/2018 | Sookraj |
| 2018/0282251 A1 | 10/2018 | Sookraj |
| 2018/0305286 A1 | 10/2018 | Sookraj |
| 2018/0305289 A1 | 10/2018 | Sookraj et al. |
| 2018/0354881 A1 | 12/2018 | Farmer et al. |
| 2018/0354882 A1 | 12/2018 | Sookraj |
| 2019/0002293 A1 | 1/2019 | Sookraj et al. |
| 2019/0002385 A1 | 1/2019 | Sookraj et al. |
| 2019/0030520 A1 | 1/2019 | Lee |
| 2019/0031592 A1 | 1/2019 | Sookraj et al. |
| 2019/0047972 A1 | 2/2019 | Sookraj |
| 2019/0071538 A1 | 3/2019 | Sookraj |
| 2019/0076834 A1 | 3/2019 | Sookraj |
| 2019/0076835 A1 | 3/2019 | Sookraj |
| 2019/0106532 A1 | 4/2019 | Sookraj |

FOREIGN PATENT DOCUMENTS

| | | |
|---|---|---|
| WO | 2012/030619 A1 | 3/2012 |
| WO | 2012/051219 A2 | 4/2012 |
| WO | 2012/158573 A1 | 11/2012 |
| WO | 2013/063191 A1 | 5/2013 |
| WO | 2013/122905 A1 | 8/2013 |
| WO | 2013/126375 A1 | 8/2013 |
| WO | 2009155086 | 10/2013 |
| WO | 2014/004858 A1 | 1/2014 |
| WO | 2014/008232 A2 | 1/2014 |
| WO | 2015/085295 A2 | 6/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/023777 A1 | 2/2017 |
| WO | 2017/023820 A1 | 2/2017 |
| WO | 2017/165323 A1 | 9/2017 |
| WO | 2017/165344 A1 | 9/2017 |
| WO | 2017/165345 A1 | 9/2017 |
| WO | 2018/085251 A1 | 5/2018 |
| WO | 2018/085254 A1 | 5/2018 |
| WO | 2018/106824 A1 | 6/2018 |
| WO | 2018/107185 A1 | 6/2018 |
| WO | 2018/136638 A1 | 7/2018 |
| WO | 2018/144998 A1 | 8/2018 |
| WO | 2018/170006 A1 | 9/2018 |
| WO | 2018/200466 A1 | 11/2018 |
| WO | 2018/200471 A1 | 11/2018 |
| WO | 2019/006366 A1 | 1/2019 |
| WO | 2019/006377 A1 | 1/2019 |
| WO | 2019/050649 A1 | 3/2019 |
| WO | 2019/051184 A1 | 3/2019 |
| WO | 2019/070981 A1 | 4/2019 |

OTHER PUBLICATIONS

Iraq Patent Application No. 486/2018, filed on Sep. 6, 2018, titled "Acrylonitrile Compounds and Other Nitrile Compounds, and Methods of Producing and Using Thereof".

Park et al., "Precursors and Manufacturing of Carbon Fibers", Chapter-2, Carbon Fibers, vol. 210, 2015, pp. 31-66.

Schechtman et al., "Chemical Synthesis of Isotactic Poly(3-Hydroxyalkanoates)", Polymer Preprints, Division of Polymer Chemistry, Inc., vol. 40, No. 1, 1999, pp. 508-509.

Smith et al., "March's Advanced Organic Chemistry: Reactions, Mechanisms and Structure", Sixth Edition, A John Wiley & Sons, Inc., 2007, 2374 pages.

Taiwanese Patent Application No. 107131599, filed on Sep. 7, 2018, titled "Acrylonitrile Compounds and Other Nitrile Compounds, and Methods of Producing and Using Thereof".

U.S. Appl. No. 62/690,783, filed Jun. 27, 2018, titled "Amide and Nitrile Compounds and Methods of Producing and Using Thereof".

Organic Chemistry—Title Page and Table of Contents, Thomas Sorrell, University Science Books, Sausalito, 1999.

Smith and March March's Advanced Organic Chemistry—Title Page and Table of Contents, 5th Edition, John Wiley & Sons, Inc., New York, 2001.

Journal of the American Chemical Society (2002), 124(51), 15239-15248.

Macromolecules, vol. 24, No. 20, pp. 5732-5733.

Journal of Polymer Science, Part A-1, vol. 9, No. 10, pp. 2775-2787.

Macromolecules, vol. 23, No. 13, pp. 3206-3212.

Macromolecules, vol. 21, No. 9, pp. 2657-2668.

ACRYLONITRILE DERIVATIVES FROM EPOXIDE AND CARBON MONOXIDE REAGENTS

CROSS-REFERENCES

The present application claims benefit from U.S. Application No. 62/527,340 filed Jun. 30, 2017, which is hereby incorporated by reference in its entirety as if fully restated herein.

FIELD OF THE INVENTION

This invention generally relates to reactor systems and processes for producing acrylonitrile and acrylonitrile derivatives. Specifically, the reactor systems and processes provide high-purity acrylonitrile and acrylonitrile derivatives through a series of reactions beginning with epoxide and carbon monoxide reagents. Advantageously, preferred embodiments of the present invention provide for versatile production of acrylonitrile and acrylonitrile derivatives from renewable epoxides and carbon monoxide feed sources.

BACKGROUND OF THE INVENTION

The term "carbonylation" generally refers to chemical reactions that introduce carbon monoxide molecules into other organic and inorganic substrate molecules. Carbonylation results in a substrate molecule gaining a carbonyl (C=O) functional group. Carbonylation reactions are important in industrial chemistry and are becoming a more important building block for fine and bulk chemicals. Specifically, catalytic carbonylation of cyclic compounds including epoxides, aziridines, thiiranes, oxetanes, lactones, lactams, and analogous compounds is useful for the synthesis of the ring expanded products of such compounds.

Further commercial and industrial benefit may result in modifying cyclic compounds through a process known as ring opening polymerization which is a form of chain-growth polymerization. In ring opening polymerization, the terminal end of a polymer chain acts as a reactive center where further cyclic monomers can react by opening cyclic rings and forming a longer polymer chain. Under certain conditions, ring-opening polymerization can proceed via radical, anionic or cationic polymerization. Certain beta-lactone, such as beta-butyrolactone, beta-valerolactone, beta-heptanolactone, beta-tridecanolactone, cis-3,4-dimethyloxetan-2-one, 4-(butoxymethyl)-2-oxetanone, 4-[[[(1,1-dimethylethyl)dimethylsilyl]oxy]methyl]-2-oxetanone, and 4-[(2-propen-1-yloxy)methyl]-2-oxetanone, 4-[(benzoyloxy)methyl]-2-oxetanone to name a few, may undergo ring opening polymerization to produce certain polylactones.

Polylactones such as polypropiolactone, polylactide, polyglycolide, and polycaprolactone are generally biodegradable aliphatic polyesters which may be comprised bio-based monomers. The polylactones are generally stable, have low toxicity, and may be easily transported and stored at remote locations. Recent advances in the carbonylation of epoxides—such as in U.S. Pat. No. 6,852,865—and the ring opening polymerization of beta-propiolactone intermediates has provided more efficient synthetic routes to polylactones. The recent advances in production combined with the physical and chemical properties make polylactones ideal for many commercial and industrial applications. However, conventional processes may be less effective at producing highly pure polylactones. Certain polylactones may be thermally decomposed through a process known as thermolysis.

Generally, thermolysis is a chemical decomposition process in which heat causes the cleavage of one or more covalent bonds. In at least one mechanism for thermolysis of polymers, heat converts a polymer of chain length n into a polymer of chain length n−1 and produces a molecule of vinyl organic acid.

Ammoxidation is a chemical process for the production of nitriles using ammonia and oxygen, usually from substrates such as alkenes. Ammoxidation of alkenes exploits weak covalent bonds that are located in the allylic position of unsaturated hydrocarbons. Benzylic covalent bonds are also susceptible to ammoxidation.

SUMMARY OF THE INVENTION

There exists a need for innovative reactor systems and processes by which higher purity acrylonitrile and acrylonitrile derivatives may be produced through a series of chemical reactions from epoxide and carbon monoxide reagents. For the purposes of this invention, the term "acrylonitrile products" refers to acrylonitrile and/or acrylonitrile derivatives.

There exists a need for innovative reactor systems and processes that produce one or more acrylonitrile products.

One object of the present invention is to provide for the processes which may produce one or more acrylonitrile products.

Another object of the present invention is to provide for the reactor systems which may be configured to produce highly pure acrylonitrile products through the processes of the present invention.

In preferred aspects of the present invention, the reactor systems and processes of the present invention are customizable and/or configurable for performing a series of chemical reactions including carbonylation, polymerization, thermolysis, esterification, and ammoxidation. In preferred aspects of the present invention, the acrylonitrile products may be wholly or partially comprised of reagents from bio-based and/or renewable sources.

In preferred embodiments, the reactor systems of the present invention may provide for carbonylation of epoxide reagents with carbon monoxide reagents to produce beta-lactone intermediates which may be directly converted to organic acids or undergo ring opening polymerization to produce polylactone products. The reactor systems of the present invention may be configured to provide heat for thermolysis to decompose the polylactone products and produce organic acid products. In certain embodiments, the reactor systems may be configured for esterification of the organic acid products to produce ester products. The reactor systems may be configured for ammoxidation of the organic acid products and/or the ester products to produce acrylonitrile products. Advantageously, polylactone products may be more safely transported from a reactor in one location to a reactor in another remote location for theremolysis.

In preferred embodiments, the reactor systems and processes overcome the deficiencies of conventional systems by providing for carbonylation of a broad range of epoxide reagents with carbon monoxide reagents to form a broad range of beta-lactone intermediates. In preferred aspects of this invention at least a portion of the epoxide reagents and/or carbon monoxide reagents may be derived from bio-base and/or renewable sources. Advantageously, the versatile reactor systems and processes of the present invention may be configured to provide a broad range of acrylonitrile products to meet demands driven by environmental concerns, regulatory changes, consumer trends, and/or production costs to name a few.

In preferred embodiments of the present invention, the reactor systems and processes may include at least one reaction vessel defining one or more feed stream inlets and one or more product stream outlets. In certain preferred embodiments, the at least one reaction vessel may define a waste stream outlet, a carbonylation section, a polymerization section, a thermolysis section, a separation section, a esterification section, and/or an ammoxidation section. In certain preferred embodiments, the at least one reaction vessel may include a heater and/or a mixer. In certain embodiments, the at least one reaction vessel may be configured for continuous production of beta-lactone intermediates polylactone products, and/or organic acids by introducing material to the at least one reaction vessel through the at least one feed stream inlet at a rate approximately equal to the rate at which material is removed through the at least one product stream outlets. In certain embodiments, one or more reaction vessels may be in the same geographic location such as a building, facility, compound, property, and/or municipality. In certain other embodiments, reaction vessels may be located at a primary location and one or more secondary locations which may be remote in distance from the primary location.

In preferred embodiments of the present invention, the processes comprise the following steps: introducing an epoxide reagent and a carbon monoxide reagent to at least one reaction vessel through at least one feed stream inlet; contacting the epoxide reagent and carbon monoxide reagent with a carbonylation catalyst in the at least one reaction vessel to produce a beta-lactone intermediate; polymerizing the beta-lactone intermediate with an initiator in the presence of a metal cation in the at least one reaction vessel to produce a polylactone product; heating the polylactone product under thermolysis conditions in the at least one reaction vessel to produce an organic acid product; optionally esterifying the organic acid product to produce an ester product; and reacting the organic acid product and/or ester product with an ammonia reagent under ammoxidation conditions to produce an acrylonitrile product. Advantageously, the processes of the present invention may control the presence of contaminates, impurities, catalytic materials, and/or reagents to provide for highly pure acrylonitrile products.

While this disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

BRIEF DESCRIPTION OF THE DRAWINGS

The present invention can be better understood by reading the following detailed description of certain preferred embodiments, reference being made to the accompanying drawings in which.

DETAILED DESCRIPTION OF EMBODIMENTS

Figure 1:
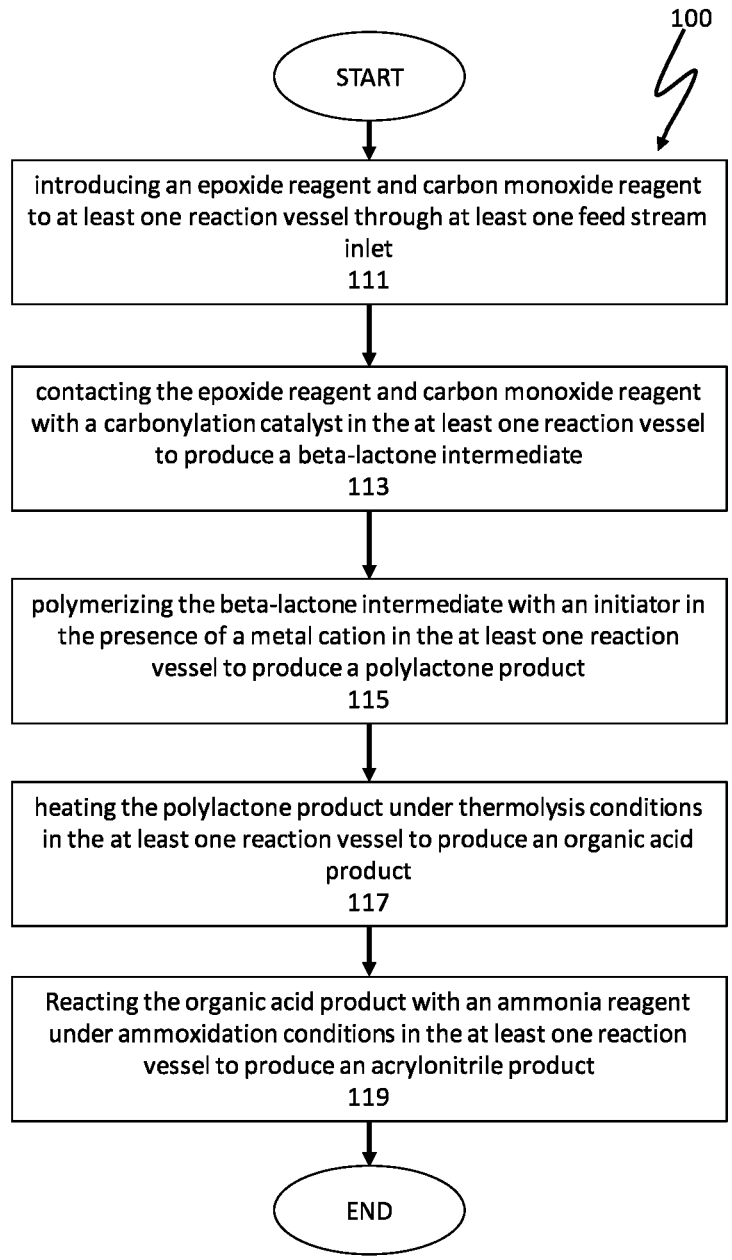
FIG. 1 illustrates steps of a preferred embodiment of a process for producing an acrylonitrile product.

The following description sets forth exemplary processes, parameters and the like. It should be recognized, however, that such description is not intended as a limitation on the scope of the present disclosure but is instead provided as a description of exemplary aspects.

DEFINITIONS

The term "polymer", as used herein, refers to a molecule of high relative molecular mass, the structure of which comprises the multiple repetition of units derived, actually or conceptually, from molecules of low relative molecular mass. In some aspects, a polymer is comprised of only one monomer species. In some aspects, a polymer is a copolymer, terpolymer, heteropolymer, block copolymer, or tapered heteropolymer of one or more epoxides.

The terms bio-content and bio-based content mean biogenic carbon also known as bio-mass derived carbon, carbon waste streams, and carbon from municipal solid waste. In some variations, bio-content (also referred to as "bio-based content") can be determined based on the following:

Bio-content or Bio-based content=[Bio (Organic) Carbon]/[Total (Organic) Carbon] 100%, as determined by ASTM D6866 (Standard Test Methods for Determining the Bio-based (biogenic) Content of Solid, Liquid, and Gaseous Samples Using Radiocarbon Analysis).

As disclosed in US 20170002136 published on Jan. 5, 2017 and filed on Jun. 30, 2016, the ASTM D6866 method allows the determination of the bio-based content of materials using radiocarbon analysis by accelerator mass spectrometry, liquid scintillation counting, and isotope mass spectrometry. When nitrogen in the atmosphere is struck by an ultraviolet light produced neutron, it loses a proton and forms carbon that has a molecular weight of 14, which is radioactive. This 14C is immediately oxidized into carbon dioxide, and represents a small, but measurable fraction of atmospheric carbon. Atmospheric carbon dioxide is cycled by green plants to make organic molecules during photosynthesis. The cycle is completed when the green plants or other forms of life metabolize the organic molecules producing carbon dioxide which is then able to return back to the atmosphere. Virtually all forms of life on Earth depend on this green plant production of organic molecules to produce the chemical energy that facilitates growth and reproduction. Therefore, the 14C that exists in the atmosphere becomes part of all life forms and their biological products. These renewably based organic molecules that biodegrade to carbon dioxide do not contribute to global warming because no net increase of carbon is emitted to the atmosphere. In contrast, fossil fuel-based carbon does not have the signature radiocarbon ratio of atmospheric carbon dioxide. See WO 2009/155086, incorporated herein by reference.

The application of ASTM D6866 to derive a "bio-based content" is built on the same concepts as radiocarbon dating, but without use of the age equations. The analysis is performed by deriving a ratio of the amount of radiocarbon (14C) in an unknown sample to that of a modern reference standard. The ratio is reported as a percentage, with the units "pMC" (percent modern carbon). If the material being analyzed is a mixture of present day radiocarbon and fossil carbon (containing no radiocarbon), then the pMC value obtained correlates directly to the amount of bio-based material present in the sample. The modern reference standard used in radiocarbon dating is a NIST (National Institute of Standards and Technology) standard with a known radiocarbon content equivalent approximately to the year AD 1950. The year AD 1950 was chosen because it represented a time prior to thermonuclear weapons testing which introduced large amounts of excess radiocarbon into the atmosphere with each explosion (termed "bomb carbon"). The AD 1950 reference represents 100 pMC. "Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. The distribution of bomb carbon has gradually decreased over time, with today's value being near 107.5 pMC. As a result, a fresh biomass material, such as corn, could result in a radiocarbon signature near 107.5 pMC.

Petroleum-based carbon does not have the signature radiocarbon ratio of atmospheric carbon dioxide. Research has noted that fossil fuels and petrochemicals have less than about 1 pMC, and typically less than about 0.1 pMC, for example, less than about 0.03 pMC. However, compounds derived entirely from renewable resources have at least about 95 percent modern carbon (pMC), they may have at least about 99 pMC, including about 100 pMC.

Combining fossil carbon with present day carbon into a material will result in a dilution of the present day pMC content. By presuming that 107.5 pMC represents present day bio-based materials and 0 pMC represents petroleum derivatives, the measured pMC value for that material will reflect the proportions of the two component types. A material derived 100% from present day biomass would give a radiocarbon signature near 107.5 pMC. If that material were diluted with 50% petroleum derivatives, it would give a radiocarbon signature near 54 pMC.

A bio-based content result is derived by assigning 100% equal to 107.5 pMC and 0% equal to 0 pMC. In this regard, a sample measuring 99 pMC will give an equivalent bio-based content result of 93%.

Assessment of the materials described herein according to the present embodiments is performed in accordance with ASTM D6866 revision 12 (i.e. ASTM D6866-12), the entirety of which is herein incorporated by reference. In some embodiments, the assessments are performed according to the procedures of Method B of ASTM-D6866-12. The mean values encompass an absolute range of 6% (plus and minus 3% on either side of the bio-based content value) to account for variations in end-component radiocarbon signatures. It is presumed that all materials are present day or fossil in origin and that the desired result is the amount of bio-based carbon "present" in the material, not the amount of bio-material "used" in the manufacturing process.

Other techniques for assessing the bio-based content of materials are described in U.S. Pat. Nos. 3,885,155, 4,427,884, 4,973,841, 5,438,194, and 5,661,299, and WO 2009/155086, each of which is incorporated herein by reference.

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In some aspects, aliphatic groups contain 1-12 carbon atoms. In some aspects, aliphatic groups contain 1-8 carbon atoms. In some aspects, aliphatic groups contain 1-6 carbon atoms. In some aspects, aliphatic groups contain 1-5 carbon atoms, in some aspects, aliphatic groups contain 1-4 carbon atoms, in yet other aspects aliphatic groups contain 1-3 carbon atoms, and in yet other aspects, aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In some aspects, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some aspects, the cycloalkyl has 3-6 carbons. Representative carbocyles include cyclopropane, cyclobutane, cyclopentane, cyclohexane, bicyclo[2,2,1]heptane, norbornene, phenyl, cyclohexene, naphthalene, and spiro[4.5]decane. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some aspects, a carbocyclic group is bicyclic. In some aspects, a carbocyclic group is tricyclic. In some aspects, a carbocyclic group is polycyclic.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In some aspects, alkyl groups contain 1-8 carbon atoms. In some aspects, alkyl groups contain 1-6 carbon atoms. In some aspects, alkyl groups contain 1-5 carbon atoms, in some aspects, alkyl groups contain 1-4 carbon atoms, in yet other aspects, alkyl groups contain 1-3 carbon atoms, and in yet other aspects alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In some aspects, "aryl" refers to an aromatic ring system which includes, but is not limited to, phenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned may include those that result in the formation of stable or chemically feasible compounds. The term "stable", as used herein, refers to compounds that are not substantially altered when subjected to conditions to allow for their production, detection, and, in some aspects, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

As used herein, the term "catalyst" refers to a substance the presence of which increases the rate of a chemical reaction, while not being consumed or undergoing a permanent chemical change itself.

Renewable sources means a source of carbon and/or hydrogen obtained from biological life forms that can replenish itself in less than one hundred years.

Renewable carbon means carbon obtained from biological life forms that can replenish itself in less than one hundred years.

Recycled sources mean carbon and/or hydrogen recovered from a previous use in a manufactured article.

Recycled carbon means carbon recovered from a previous use in a manufactured article.

As used herein, the term "about" preceding one or more numerical values means the numerical value ±5%. It should be understood that reference to "about" a value or parameter herein includes (and describes) aspects that are directed to that value or parameter per se. For example, description referring to "about x" includes description of "x" per se.

Further, it should be understood that reference to "between" two values or parameters herein includes (and describes) aspects that include those two values or parameters per se. For example, description referring to "between x and y" includes description of "x" and "y" per se.

The mass fractions disclosed herein can be converted to wt % by multiplying by 100.

EXEMPLARY EMBODIMENTS

In preferred embodiments of the present invention, the reactor systems and processes may produce acrylonitrile products from epoxide regents, carbon monoxide reagents, and ammonia reagents through a series of reactions. One exemplary embodiment of a series of reactions that produces a highly pure acrylonitrile product is as follows:

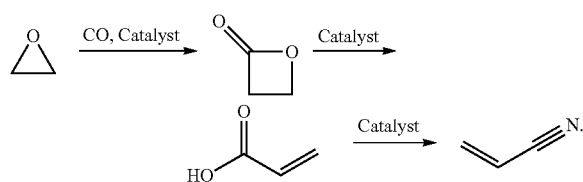

Another exemplary embodiment is as follows:

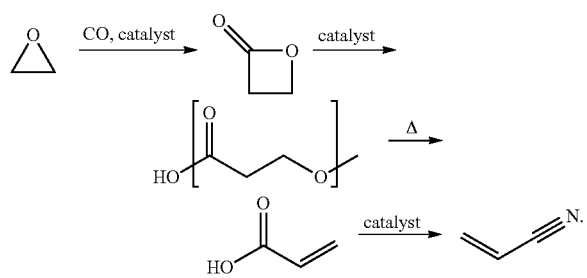

FIG. 1 illustrates a preferred embodiment of the present invention directed to producing acrylonitrile products comprising the following steps: introducing an epoxide reagent and a carbon monoxide reagent to at least one reaction vessel through at least one feed stream inlet in a step 111; contacting the epoxide reagent and carbon monoxide reagent with a carbonylation catalyst in the at least one reaction vessel to produce a beta-lactone intermediate in a step 113; polymerizing the beta-lactone intermediate with an initiator in the presence of a metal cation in the at least one reaction vessel to produce a polylactone product in a step 115; heating the polylactone product under thermolysis conditions in the at least one reaction vessel to produce an organic acid product in a step 117; and reacting the organic acid product with an ammonia reagent under ammoxidation conditions in the at least one reaction vessel to produce an acrylonitrile product in a step 119. In certain preferred embodiments, the processes of the present invention may be performed in two or more reaction vessels. Advantageously, the processes of the present invention may control the presence of contaminates, impurities, catalytic materials, and/or reagents to provide for highly pure acrylonitrile products. In some embodiments, a step for esterification of the organic acid product may be performed prior to ammoxidation. In certain preferred embodiments, the processes of the present invention may produce an organic acid product directly from a beta-lactone intermediate.

In preferred embodiments of the present invention, the processes may include a step for introducing an epoxide reagent and carbon monoxide reagent to at least reaction vessel through at least one feed stream inlet in a step 111. The epoxide reagent and/or carbon reagent may enter the at least one reaction vessel with mechanical assistance and/or by natural forces. In some embodiments, a mechanical pump may assist in introducing the at least one epoxides reagent and carbon monoxide reagent to the at least one reaction vessel through the at least one feed stream inlet. In some embodiments, epoxide reagent and carbon monoxide reagent may be stored at a higher pressure than the at least one reaction vessel so that the epoxide reagent and carbon monoxide reagents may enter the at least one reaction vessel by the natural equalizing of pressure.

In certain preferred embodiments, the processes of the present invention may include an epoxide reagent and one or more carbon monoxide reagent may be fed into the at least one reaction vessel at an amount sufficient for carbonylation under superatmospheric pressure. In certain embodiments, the epoxide reagent and carbon monoxide reagent are provided at a pressure in the range from about 50 psi (350 kPa) to about 5000 psi (35 MPa). In certain embodiments, the epoxide reagent and carbon monoxide reagent are provided at a pressure from about 50 psi (350 kPa) to about 1000 psi (7 Mpa), at a pressure from about 50 psi (350 kPa) to about 500 psi (3.5 Mpa), at a pressure from about 100 psi (700 kPa) to about 400 psi (2.8 Mpa), or at a pressure of about 200 psi (1.4 Mpa). In certain embodiments, the epoxide reagent and carbon monoxide reagent are provided under an atmosphere having a partial pressure of CO of about 200 psi (1.4 Mpa). The superatmospheric pressure of the carbon monoxide reagent may be provided in the form of pure carbon monoxide, or by introducing a gas mixture containing two or more sources of carbon monoxide. In other embodiments, the epoxide reagent and carbon monoxide reagent may be provided mixed with one or more inert gases. In certain preferred embodiments, the epoxide reagent and carbon monoxide reagent may be comprised of bio-based carbon.

In some embodiments, the processes of the present invention may introduce the epoxide reagent and carbon monoxide reagent at least about 1000 kg/hr, at least about 2000 kg/hr, at least about 5000 kg/hr, at least about 10000 kg/hr, or at least about 16000 kg/hr. In some embodiments, the processes of the present invention may introduce the epoxide reagent and carbon monoxide reagent at least about 30 kmol/hr, or at least about 60 kmol/hr. In some embodiments, the epoxide reagent and carbon monoxide reagent are introduced at about 1000 kg/hr to about 16000 kg/hr, about 2000 kg/hr to about 16000 kg/hr, or about 4000 kg/hr to about 16000 kg/hr. In some embodiments, the processes of the present invention may introduce the epoxide reagent and the carbon monoxide reagent at least about 30 kmol/hr or at least about 500 kmol/hr. In some embodiments, the flow rate from the epoxide reagent and/or the carbon monoxide reagent is set to about the stoichiometric value for the carbonylation reaction, to about 5% higher than the stoichiometric value, to about 10% higher than the stoichiometric value, to about 15% higher than the stoichiometric value, or to about 20% higher than the stoichiometric value.

In preferred embodiments, the processes of the present invention include a step for contacting the epoxide reagent and carbon monoxide reagent with a carbonylation catalyst in at least one reaction vessel to produce a beta-lactone intermediate in a step of 113. Within the at least one reaction vessel, the epoxide reagent and carbon monoxide reagent contact the carbonylation catalyst to produce a beta-lactone intermediate, as generally depicted in the reaction scheme below:

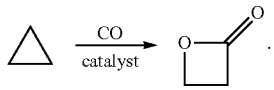

Carbonylation may utilize a metal carbonyl-Lewis acid catalyst such as those described in U.S. Pat. No. 6,852,865. In other aspects, the carbonylation step is performed with one or more of the carbonylation catalysts disclosed in U.S. patent application Ser. Nos. 10/820,958; and 10/586,826. In other aspects, the carbonylation step is performed with one or more of the catalysts disclosed in U.S. Pat. Nos. 5,310,948; 7,420,064; and 5,359,081. Additional catalysts for the carbonylation of epoxides are discussed in a review in Chem. Commun., 2007, 657-674. The entirety of each of the preceding references is incorporated herein by reference.

In certain embodiments, the carbonylation catalyst may be fed to the at least one reaction vessels in a manner similar to the epoxide reagent and carbon monoxide reagent. The carbonylation catalyst can be pumped under carbon monoxide blanket to help ensure stability of the catalyst and can be cooled, optionally along with the feed, below ambient temperature to ensure stability. The carbonylation catalyst can be introduced to the carbonylation section of the at least one reaction vessel as a solid or in solution of solvent such as hexane or tetrahydrofuran.

In certain preferred embodiments, the step for contacting the epoxide reagent and carbon monoxide reagent with the carbonylation catalyst includes a carbonylation catalyst comprising a metal carbonyl compound. Typically, a single metal carbonyl compound is provided, but in some embodiments, mixtures of two or more metal carbonyl compounds are provided. Thus, when a provided metal carbonyl compound "comprises", e.g., a neutral metal carbonyl compound, it is understood that the provided metal carbonyl compound can be a single neutral metal carbonyl compound, or a neutral metal carbonyl compound in combination with one or more metal carbonyl compounds. Preferably, the provided metal carbonyl compound is capable of ring-opening an epoxide and facilitating the insertion of carbon monoxide into the resulting metal carbon bond.

In some embodiments, a carbonylation catalyst comprising a metal carbonyl compound comprises an anionic metal carbonyl moiety. In other embodiments, a carbonylation catalyst comprising a metal carbonyl compound comprises a neutral metal carbonyl compound. In still other embodiments, a metal carbonyl compound comprises a metal carbonyl hydride or a hydrido metal carbonyl compound.

In some embodiments, a carbonylation catalyst comprising a metal carbonyl compound further comprises an anionic metal carbonyl species. The anionic metal carbonyl species may have the general formula [QdM'e(CO)w]y-, where Q is any ligand and need not be present, M' is a metal atom, d is an integer between 0 and 8 inclusive, e is an integer between 1 and 6 inclusive, w is a number such as to provide the stable anionic metal carbonyl complex, and y is the charge of the anionic metal carbonyl species. In some embodiments, the anionic metal carbonyl has the general formula [QM'(CO)w]y-, where Q is any ligand and need not be present, M' is a metal atom, w is a number such as to provide the stable anionic metal carbonyl, and y is the charge of the anionic metal carbonyl.

In some embodiments, a carbonylation catalyst comprising an anionic metal carbonyl species include a monoanionic carbonyl complexes of metals from groups 5, 7 or 9 of the periodic table or dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, but are not limited to: [Co(CO)4]-, [Ti(CO)6]2-[V(CO)6]-[Rh(CO)4]-, [Fe(CO)4]2-[Ru(CO)4]2-, [Os(CO)4]2-[Cr2(CO)10]2-[Fe2(CO)8]2-[Tc(CO)5]-[Re(CO)5]- and [Mn(CO)5]-. In some embodiments, the anionic metal carbonyl comprises [Co(CO)4]-. In some embodiments, a mixture of two or more anionic metal carbonyl complexes may be present in the carbonylation catalysts used in reactor systems and processes of the present invention.

In embodiments where the provided metal carbonyl compound is an anionic species, one or more cations must also necessarily be present. In some variations, no particular constraints on the identity of such cations. In some embodiments, the cation associated with an anionic metal carbonyl compound comprises a reaction component of another category described herein. For example, in some embodiments, the metal carbonyl anion is associated with a cationic Lewis acid. In other embodiments, a cation associated with a provided anionic metal carbonyl compound is a simple metal cation such as those from Groups 1 or 2 of the periodic table (e.g., Na+, Li+, K+, Mg2+ and the like). In other embodiments, a cation associated with a provided anionic metal carbonyl compound is a bulky non electrophilic cation such as an 'onium salt' (e.g., Bu4N+, PPN+, Ph4P+Ph4As+, and the like). In other embodiments, a metal carbonyl anion is associated with a protonated nitrogen compound (e.g., a cation may comprise a compound such as MeTBD-H+, DMAP-H+, DABCO-H+, DBU-H+ and the like). In some embodiments, compounds comprising such protonated nitrogen compounds are provided as the reaction product between an acidic hydrido metal carbonyl compound and a basic nitrogen-containing compound (e.g., a mixture of DBU and HCo(CO)4).

In certain preferred embodiments, a carbonylation catalyst utilized in the reactor systems and processes described herein comprises a neutral metal carbonyl compound. In some embodiments, such neutral metal carbonyl compounds have the general formula QdM'e(CO)w', where Q is any ligand and need not be present, M' is a metal atom, d is an integer between 0 and 8 inclusive, e is an integer between 1 and 6 inclusive, and w' is a number such as to provide the stable neutral metal carbonyl complex. In some embodiments, the neutral metal carbonyl has the general formula QM'(CO)w'. In some embodiments, the neutral metal carbonyl has the general formula M'(CO)w'. In some embodiments, the neutral metal carbonyl has the general formula QM'2(CO)w'. In some embodiments, the neutral metal carbonyl has the general formula M'2(CO)w'. Suitable neutral metal carbonyl compounds include, but are not limited to: Ti(CO)7; V2(CO)12; Cr(CO)6; Mo(CO)6; W(CO)6 Mn2(CO)10, Tc2(CO)10, and Re2(CO)10 Fe(CO)5, Ru(CO)5 and Os(CO)5 Ru3(CO)12, and Os3(CO)12 Fe3(CO)12 and Fe2(CO)9 Co4(CO)12, Rh4(CO)12, Rh6(CO)16, and Ir4(CO)12 Co2(CO)8 Ni(CO)4.

In some embodiments, no ligands Q are present on the metal carbonyl compound. In other embodiments, one or more ligands Q are present on the metal carbonyl compound. In some embodiments, where Q is present, each occurrence of Q is selected from the group consisting of phosphine ligands, amine ligands, cyclopentadienyl ligands, heterocyclic ligands, nitriles, phenols, and combinations of two or more of these. In some embodiments, one or more of the CO ligands of any of the metal carbonyl compounds described above is replaced with a ligand Q. In some embodiments, Q is a phosphine ligand. In some embodiments, Q is a triaryl phosphine. In some embodiments, Q is trialkyl phosphine. In some embodiments, Q is a phosphite ligand. In some embodiments, Q is an optionally substituted cyclopentadienyl ligand. In some embodiments, Q is cp. In some embodiments, Q is cp*. In some embodiments, Q is an amine or a heterocycle.

In some embodiments, the carbonylation catalyst utilized in the reactor systems and processes described above further includes a Lewis acidic component. In some embodiments, the carbonylation catalyst includes an anionic metal carbonyl complex and a cationic Lewis acidic component. In some embodiments, the metal carbonyl complex includes a carbonyl cobaltate and the Lewis acidic co-catalyst includes a metal-centered cationic Lewis acid. In some embodiments, an included Lewis acid comprises a boron compound.

In some embodiments, a carbonylation catalyst including Lewis acid comprises a boron compound, the boron compound comprises a trialkyl boron compound or a triaryl boron compound. In some embodiments, an included boron compound comprises one or more boron-halogen bonds. In some embodiments, where an included boron compound comprises one or more boron-halogen bonds, the compound is a dialkyl halo boron compound (e.g., R2BX), a dihalo monoalkyl compound (e.g., RBX2), an aryl halo boron compound (e.g., Ar2BX or ArBX2), or a trihalo boron compound (e.g., BCl3 or BBr3), wherein each R is an alkyl group; each X is a halogen; and each Ar is an aromatic group.

In some embodiments, where the included Lewis acid comprises a metal-centered cationic Lewis acid, the Lewis acid is a cationic metal complex. In some embodiments, the cationic metal complex has its charge balanced either in part, or wholly by one or more anionic metal carbonyl moieties. Suitable anionic metal carbonyl compounds include those described above. In some embodiments, there are 1 to 17 such anionic metal carbonyls balancing the charge of the metal complex. In some embodiments, there are 1 to 9 such anionic metal carbonyls balancing the charge of the metal complex. In some embodiments, there are 1 to 5 such anionic metal carbonyls balancing the charge of the metal complex. In some embodiments, there are 1 to 3 such anionic metal carbonyls balancing the charge of the metal complex.

In some embodiments, where carbonylation catalysts used in the reactor systems and processes of the present invention include a cationic metal complex, the metal complex has the formula [(Lc)vMb]z+, where:

Lc is a ligand where, when two or more Lc are present, each may be the same or different;

M is a metal atom where, when two M are present, each may be the same or different;

v is an integer from 1 to 4 inclusive;

b is an integer from 1 to 2 inclusive; and z is an integer greater than 0 that represents the cationic charge on the metal complex.

In some embodiments, provided Lewis acids conform to structure I:

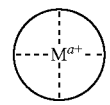

I wherein:

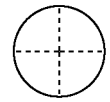

is a multidentate ligand;

M is a metal atom coordinated to the multidentate ligand;

a is the charge of the metal atom and ranges from 0 to 2; and

In some embodiments, provided metal complexes conform to structure II:

II

Where a is as defined above (each a may be the same or different), and

M1 is a first metal atom;

M2 is a second metal atom;

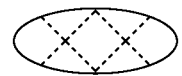

comprises a multidentate ligand system capable of coordinating both metal atoms.

For sake of clarity, and to avoid confusion between the net and total charge of the metal atoms in complexes I and II and other structures herein, the charge (a+) shown on the metal atom in complexes I and II above represents the net charge on the metal atom after it has satisfied any anionic sites of the multidentate ligand. For example, if a metal atom in a complex of formula I were Cr(III), and the ligand were porphyrin (a tetradentate ligand with a charge of −2), then the chromium atom would have a net charge of +1, and a would be 1.

Suitable multidentate ligands include, but are not limited to: porphyrin derivatives 1, salen derivatives 2, dibenzotetramethyltetraaza[14]annulene (tmtaa) derivatives 3, phthalocyaninate derivatives 4, derivatives of the Trost ligand 5, tetraphenylporphyrin derivatives 6, and corrole derivatives 7. In some embodiments, the multidentate ligand is a salen derivative. In other embodiments, the multidentate ligand is a porphyrin derivative. In other embodiments, the multidentate ligand is a tetraphenylporphyrin derivative. In other embodiments, the multidentate ligand is a corrole derivative.

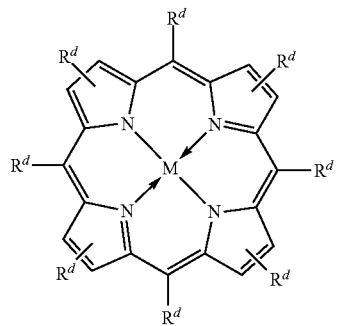

1

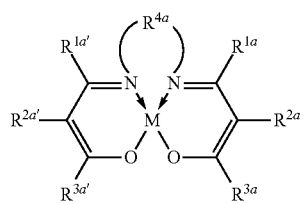

2

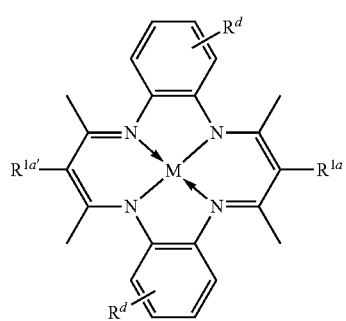

3

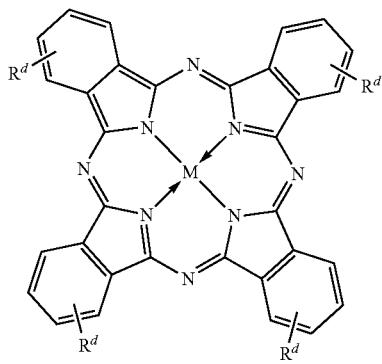

4

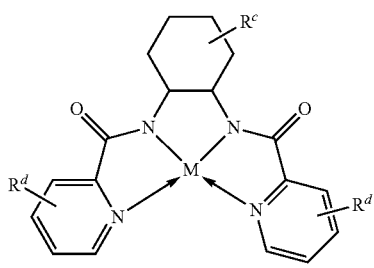

5

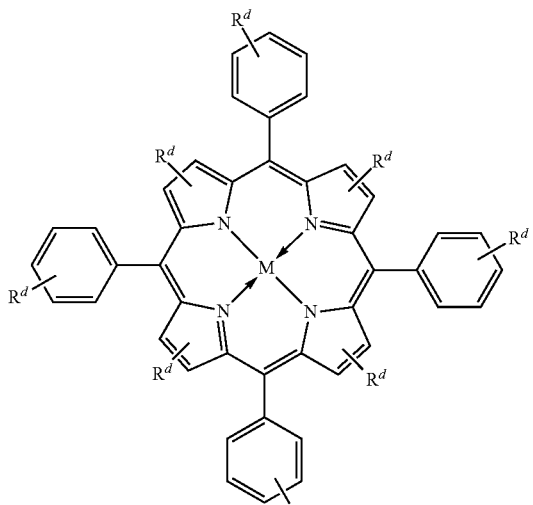

6

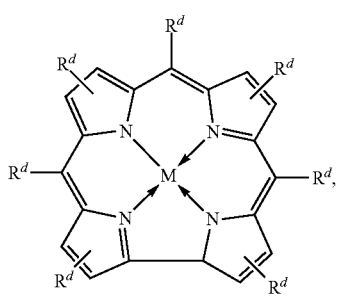

7 where each of Rc, Rd, R1a, R2a, R3a, R4a, R1a', R2a', R3a', and M, is as defined and described in the classes and subclasses herein.

In some embodiments, Lewis acids provided carbonylation catalysts used in reactor systems and processes described herein comprise metal-porphinato complexes. In some embodiments, the moiety

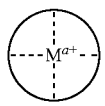

has the structure:

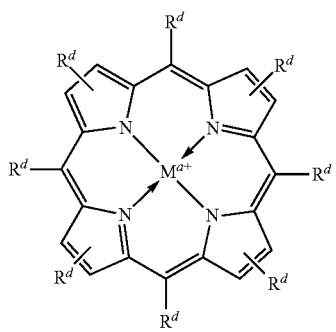

where each of M and a is as defined above and described in the classes and subclasses herein, and Rd at each occurrence is independently hydrogen, halogen, —OR4, —NRy2, —SRy, —CN, —NO2, —SO2Ry, —SORy, —SO2NRy2; —CNO, —NRySO2Ry, —NCO, —N3, —SiRy3; or an optionally substituted group selected from the group consisting of C1-20 aliphatic; C1-20 heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur, where two or more Rd groups may be taken together to form one or more optionally substituted rings.

Each Ry is independently hydrogen, an optionally substituted group selected the group consisting of acyl; carbamoyl, arylalkyl; 6- to 10-membered aryl; C1-12 aliphatic; C1-12 heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; two Ry on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each R4 is independently is a hydroxyl protecting group or Ry.

In some embodiments, the moiety

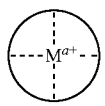

has the structure:

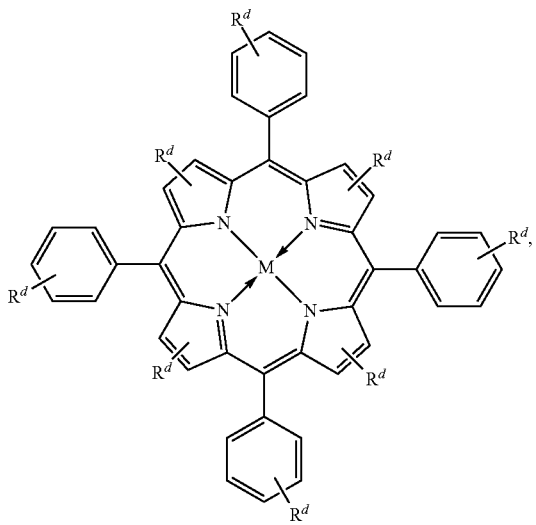

where M, a and Rd are as defined above and in the classes and subclasses herein.

In some embodiments, the moiety

has the structure:

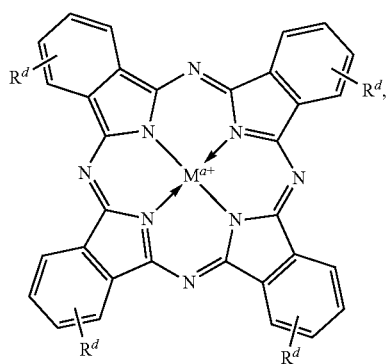

where M, a and Rd are as defined above and in the classes and subclasses herein.

In some embodiments, Lewis acids included in carbonylation catalysts used in reactor systems and processes described herein comprise metallo salenate complexes. In some embodiments, the moiety

has the structure:

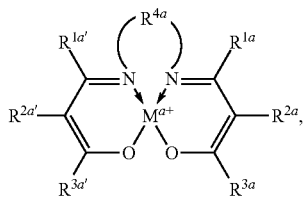

wherein:

M, and a are as defined above and in the classes and subclasses herein.

R1a, R1a', R2a, R2a', R3a, and R3a' are independently hydrogen, halogen, —OR4, —NRy2, —SRy, —CN, —NO2, —SO2Ry, —SORy, —SO2NRy2; —CNO, —NRySO2Ry, —NCO, —N3, —SiRy3; or an optionally substituted group selected from the group consisting of C1-20 aliphatic; C1-20 heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; wherein each R4, and Ry is independently as defined above and described in classes and subclasses herein, wherein any of (R2a' and R3a'), (R2a and R3a), (R1a and R2a), and (R1a' and R2a') may optionally be taken together with the carbon atoms to which they are attached to form one or more rings which may in turn be substituted with one or more Ry groups; and R4a is selected from the group consisting of:

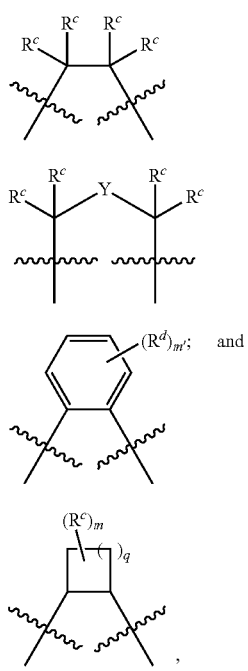

where

Rc at each occurrence is independently hydrogen, halogen, —OR4, —NRy2, —SRy, —CN, —NO2, —SO2Ry, —SORy, —SO2NRy2; —CNO, —NRySO2Ry, —NCO, —N3, —SiRy3; or an optionally substituted group selected from the group consisting of C1-20 aliphatic; C1-20 heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur;

where:

two or more Rc groups may be taken together with the carbon atoms to which they are attached and any intervening atoms to form one or more rings;

when two Rc groups are attached to the same carbon atom, they may be taken together along with the carbon atom to which they are attached to form a moiety selected from the group consisting of: a 3- to 8-membered spirocyclic ring, a carbonyl, an oxime, a hydrazine, an imine; and an optionally substituted alkene;

where R4 and Ry are as defined above and in classes and subclasses herein;

Y is a divalent linker selected from the group consisting of: —NRy-, —N(Ry)C(O)—, —C(O)NRy-, —O—, —C(O)—, —OC(O)—, —C(O)O—, —S—, —SO—, —SO2-, —C(=S)—, —C(=NRy)-, —N=N—; a polyether; a C3 to C8 substituted or unsubstituted carbocycle; and a C1 to C8 substituted or unsubstituted heterocycle;

m' is 0 or an integer from 1 to 4, inclusive;

q is 0 or an integer from 1 to 4, inclusive; and x is 0, 1, or 2.

In some embodiments, a provided Lewis acid comprises a metallo salen compound, as shown in formula Ia:

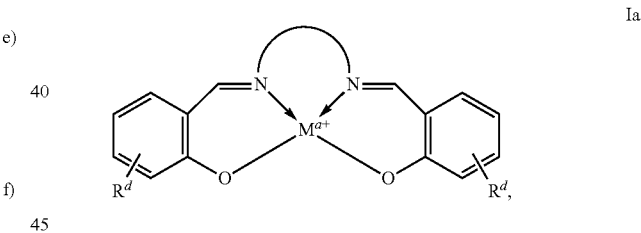

Ia wherein each of M, Rd, and a, is as defined above and in the classes and subclasses herein, represents is an optionally substituted moiety linking the two nitrogen atoms of the diamine portion of the salen ligand, where is selected from the group consisting of a C3-C14 carbocycle, a C6-C10 aryl group, a C3-C14 heterocycle, and a C5-C10 heteroaryl group; or an optionally substituted C2-20 aliphatic group, wherein one or more methylene units are optionally and independently replaced by —NRy-, —N(Ry)C(O)—, —C(O)N(Ry)-, —OC(O)N(Ry)-, —N(Ry)C(O)O—, —OC(O)O—, —O—, —C(O)—, —OC(O)—, —C(O)O—, —S—, —SO—, —SO2-, —C(=S)—, —C(=NRy)-, —C(=NORy)- or —N=N—.
In some embodiments metal complexes having formula Ia above, at least one of the phenyl rings comprising the salicylaldehyde-derived portion of the metal complex is independently selected from the group consisting of:
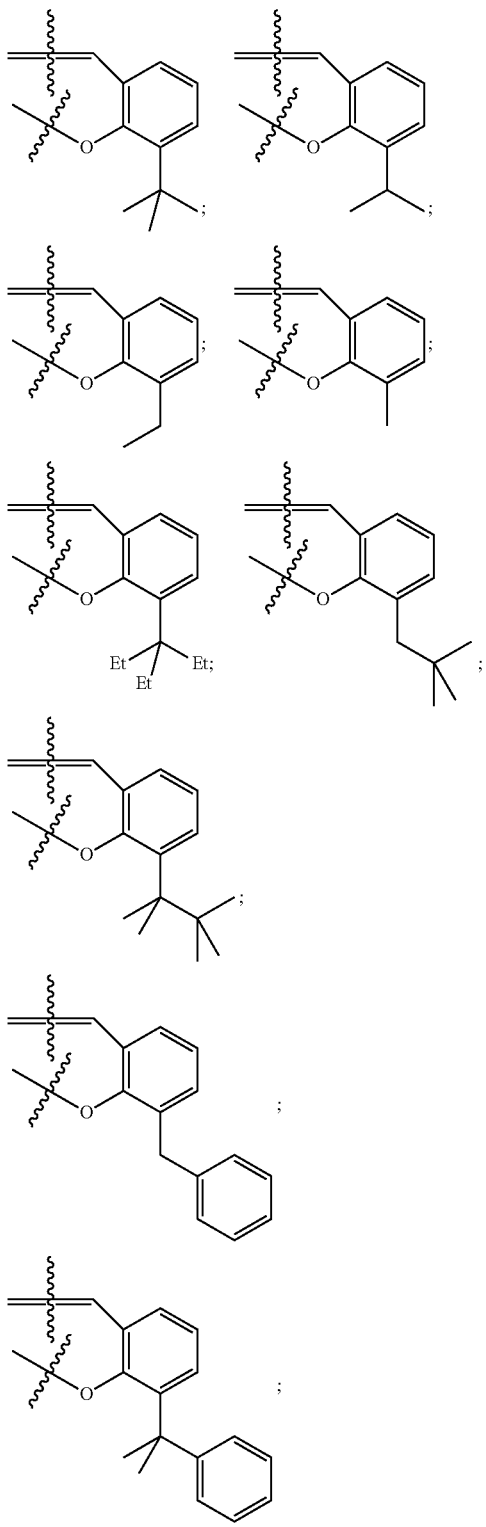
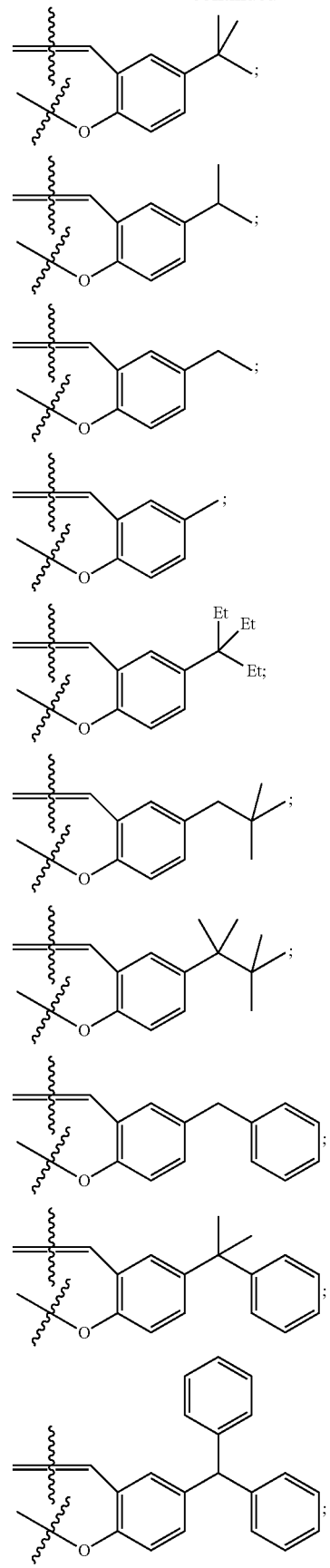

-continued
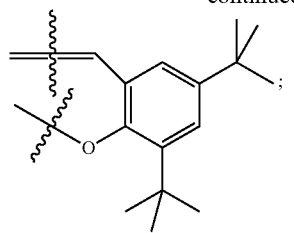
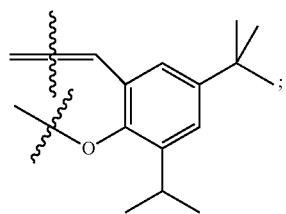
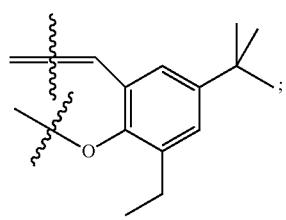
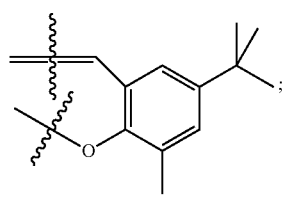
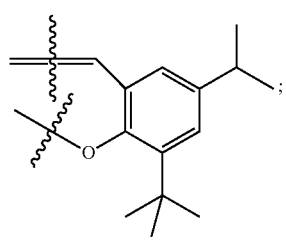
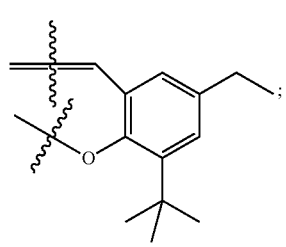
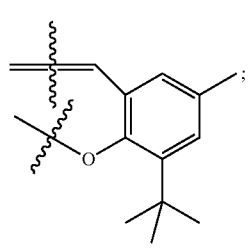
-continued
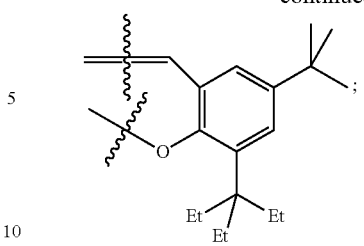
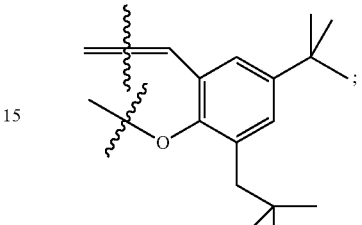
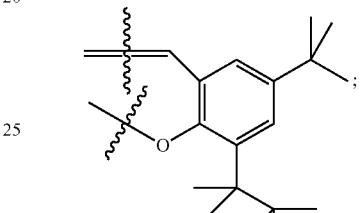
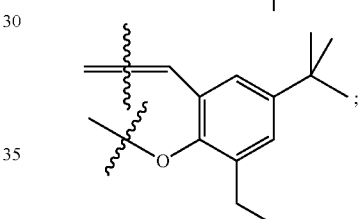
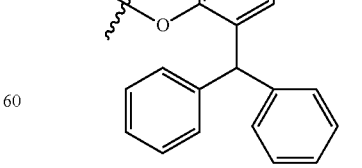
; and
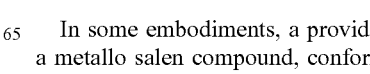
In some embodiments, a provided Lewis acid comprises a metallo salen compound, conforming to one of formulae Va or Vb:

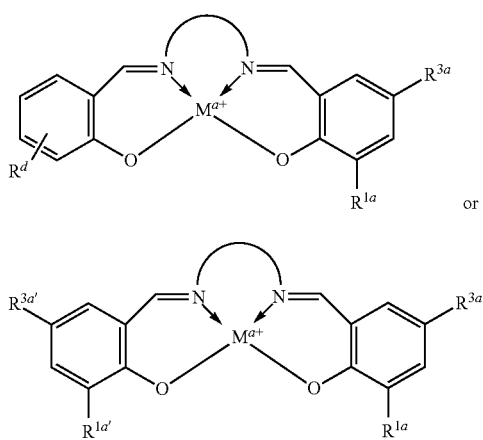

where M, a, Rd, R1a, R3a, R1a', R3a', and

are as defined above and in the classes and subclasses herein.

In some embodiments of metal complexes having formulae Va or Vb, each R1a and R3a is, independently, optionally substituted C1-C20 aliphatic.

In some embodiments, the moiety

comprises an optionally substituted 1, 2-phenyl moiety.

In some embodiments, Lewis acids included in carbonylation catalysts used in reactor systems and processes described herein comprise metal-tmtaa complexes. In some embodiments, the moiety

has the structure:

wherein M, a and Rd are as defined above and in the classes and subclasses herein, and Re at each occurrence is independently hydrogen, halogen, —OR, —NRy2, —SRy, —CN, —NO2, —SO2Ry, —SORy, —SO2NRy2; —CNO, —NRySO2Ry, —NCO, —N3, —SiRy3; or an optionally substituted group selected from the group consisting of C1-20 aliphatic; C1-20 heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur.

In some embodiments, the moiety

has the structure:

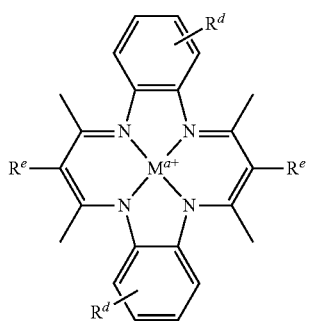

wherein each of M, a, Rc and Rd is as defined above and in the classes and subclasses herein.

In some embodiments, where carbonylation catalysts used in reactor systems and processes described herein include a Lewis acidic metal complex, the metal atom is selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium.

In some embodiments, M has an oxidation state of +2. In some embodiments, M is Zn(II), Cu(II), Mn(II), Co(II), Ru(II), Fe(II), Co(II), Rh(II), Ni(II), Pd(II) or Mg(II). In some embodiments M is Zn(II). In some embodiments M is Cu(II).

In some embodiments, M has an oxidation state of +3. In some embodiments, M is Al(III), Cr(III), Fe(III), Co(III), Ti(III) In(III), Ga(III) or Mn(III). In some embodiments M is Al(III). In some embodiments M is Cr(III).

In some embodiments, M has an oxidation state of +4. In some embodiments, M is Ti(IV) or Cr(IV).

In some embodiments, M1 and M2 are each independently a metal atom selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium. In some embodiments, M1 and M2 are the same. In some embodiments, M1 and M2 are the same metal, but have different oxidation states. In some embodiments, M1 and M2 are different metals.

In some embodiments, one or more of M1 and M2 has an oxidation state of +2. In some embodiments, M1 is Zn(II), Cu(II), Mn(II), Co(II), Ru(II), Fe(II), Co(II), Rh(II), Ni(II), Pd(II) or Mg(II). In some embodiments M1 is Zn(II). In some embodiments M1 is Cu(II). In some embodiments, M2 is Zn(II), Cu(II), Mn(II), Co(II), Ru(II), Fe(II), Co(II), Rh(II), Ni(II), Pd(II) or Mg(II). In some embodiments M2 is Zn(II). In some embodiments M2 is Cu(II).

In some embodiments, one or more of M1 and M2 has an oxidation state of +3. In some embodiments, M1 is Al(III), Cr(III), Fe(III), Co(III), Ti(III) In(III), Ga(III) or Mn(III). In some embodiments M1 is Al(III). In some embodiments M1 is Cr(III). In some embodiments, M2 is Al(III), Cr(III), Fe(III), Co(III), Ti(III) In(III), Ga(III) or Mn(III). In some embodiments M2 is Al(III). In some embodiments M2 is Cr(III).

In some embodiments, one or more of M1 and M2 has an oxidation state of +4. In some embodiments, M1 is Ti(IV) or Cr(IV). In some embodiments, M2 is Ti(IV) or Cr(IV).

In some embodiments, the metal-centered Lewis-acidic component of the carbonylation catalyst includes a dianionic tetradentate ligand. In some embodiments, the dianionic tetradentate ligand is selected from the group consisting of: porphyrin derivatives; salen derivatives; dibenzotetramethyltetraaza[14]annulene (tmtaa) derivatives; phthalocyaninate derivatives; and derivatives of the Trost ligand.

In some embodiments, the carbonylation catalyst includes a carbonyl cobaltate in combination with an aluminum porphyrin compound. In some embodiments, the carbonylation catalyst is [(TPP)Al(THF)2][Co(CO)4] where TPP stands for tetraphenylporphyrin and THF stands for tetrahydrofuran.

In some embodiments, the carbonylation catalyst includes a carbonyl cobaltate in combination with a chromium porphyrin compound.

In some embodiments, the carbonylation catalyst includes a carbonyl cobaltate in combination with a chromium salen compound. In some embodiments, the carbonylation catalyst includes a carbonyl cobaltate in combination with a chromium salophen compound.

In some embodiments, the carbonylation catalyst includes a carbonyl cobaltate in combination with an aluminum salen compound. In some embodiments, the carbonylation catalyst includes a carbonyl cobaltate in combination with an aluminum salophen compound.

In some embodiments, one or more neutral two electron donors coordinate to M, M1, or M2 and fill the coordination valence of the metal atom. In some embodiments, the neutral two electron donor is a solvent molecule. In some embodiments, the neutral two electron donor is an ether. In some embodiments, the neutral two electron donor is tetrahydrofuran, diethyl ether, acetonitrile, carbon disulfide, or pyridine. In some embodiments, the neutral two electron donor is tetrahydrofuran. In some embodiments, the neutral two electron donor is an epoxide. In some embodiments, the neutral two electron donor is an ester or a lactone.

In certain embodiments, the carbonylation catalyst includes a carbonyl cobaltate in combination with an aluminum porphyrin compound. In certain embodiments, the carbonylation catalyst includes a carbonyl cobaltate in combination with a chromium porphyrin compound. In certain embodiments, the carbonylation catalyst includes a carbonyl cobaltate in combination with a chromium salen compound. In certain embodiments, the carbonylation catalyst includes a carbonyl cobaltate in combination with a chromium salophen compound. In certain embodiments, the carbonylation catalyst includes a carbonyl cobaltate in combination with an aluminum salen compound. In certain embodiments, the carbonylation catalyst includes a carbonyl cobaltate in combination with an aluminum salophen compound.

TABLE 1 illustrated below includes Column A directed to a non-exhaustive list of epoxides which may undergo carbonylation to produce beta-lactone intermediates according to the processes of the present invention and Column B directed to a non-exhaustive list of beta-lactone intermediates which may undergo ring opening polymerization to produce polylactones according to the processes of the present invention.

Column A

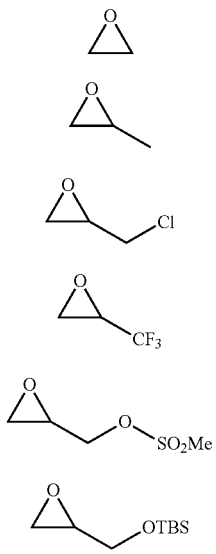

TABLE 1-continued
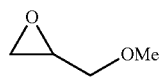
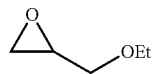
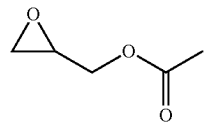
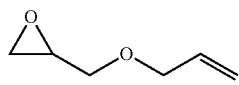
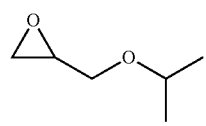
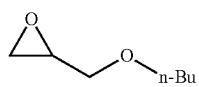
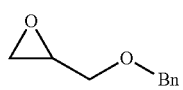
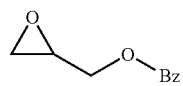
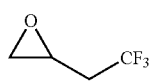
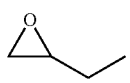
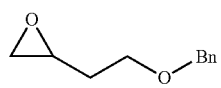
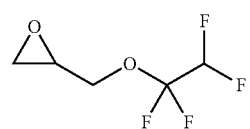 [SMILES: FC(F)C(F)(F)OCC1CO1]
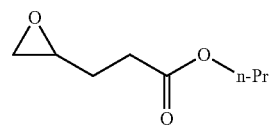
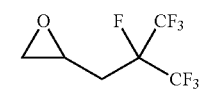
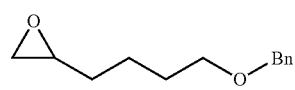 [SMILES: c1ccc(COCCCCC2CO2)cc1]

TABLE 1-continued
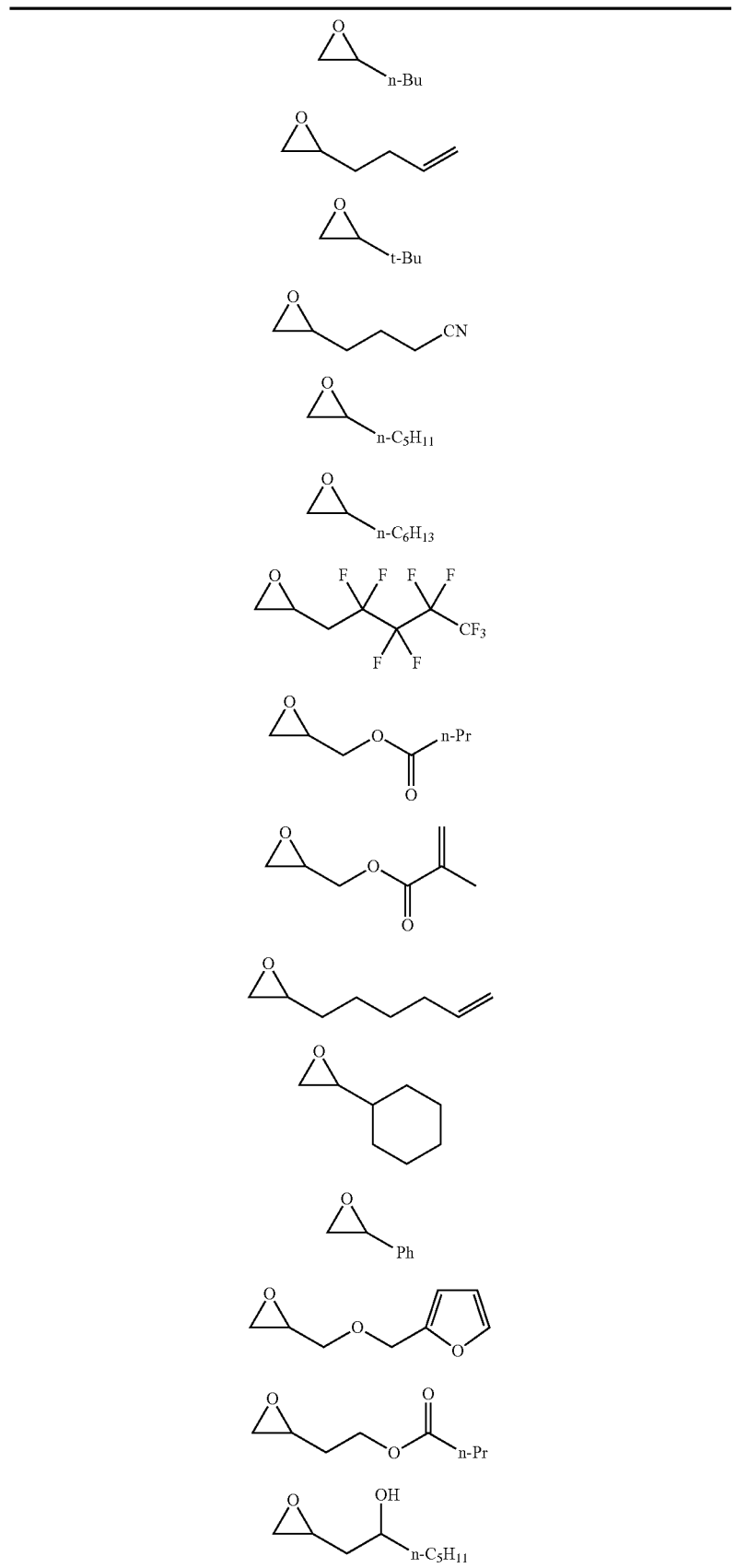

TABLE 1-continued
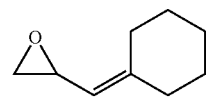
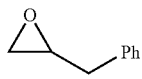
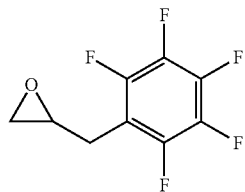 [SMILES: Fc1c(F)c(F)c(CC2CO2)c(F)c1F]
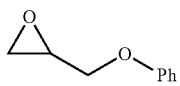
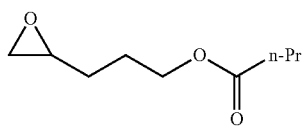
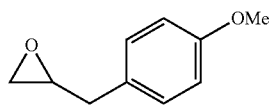
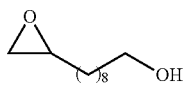
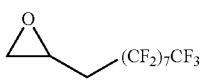
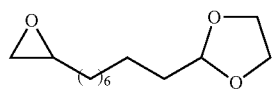
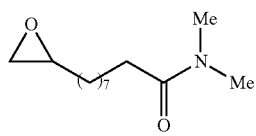
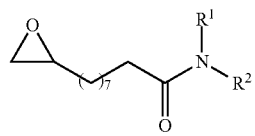
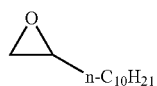

TABLE 1-continued
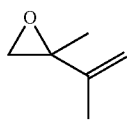
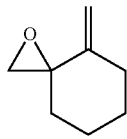
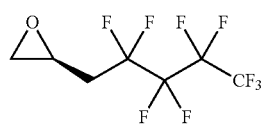 [SMILES: FC(F)(F)C(F)(F)C(F)(F)C(F)(F)C[C@H]1CO1]
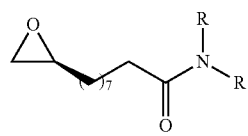
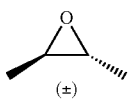
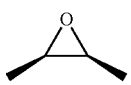
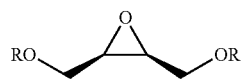
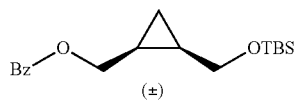
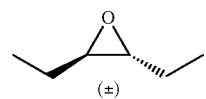
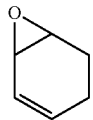
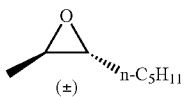

TABLE 1-continued
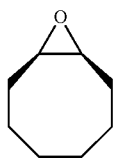
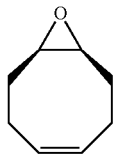
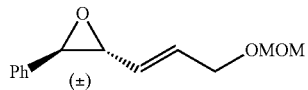
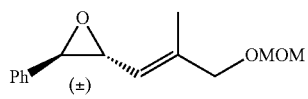
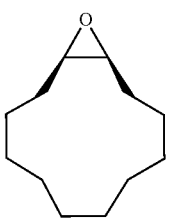 [SMILES: C1CCCCC[C@H]2O[C@H]2CCCC1]
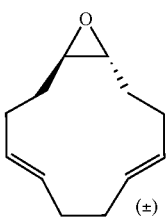 [SMILES: C1=C/CC[C@H]2O[C@@H]2CC/C=C/CC/1]
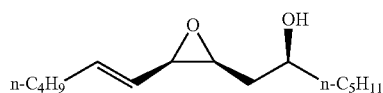
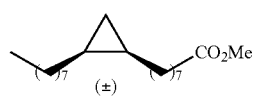
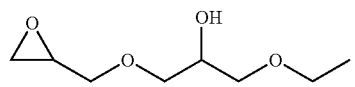
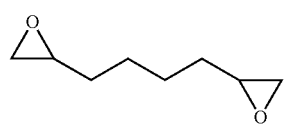
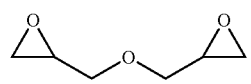

TABLE 1-continued
Column B
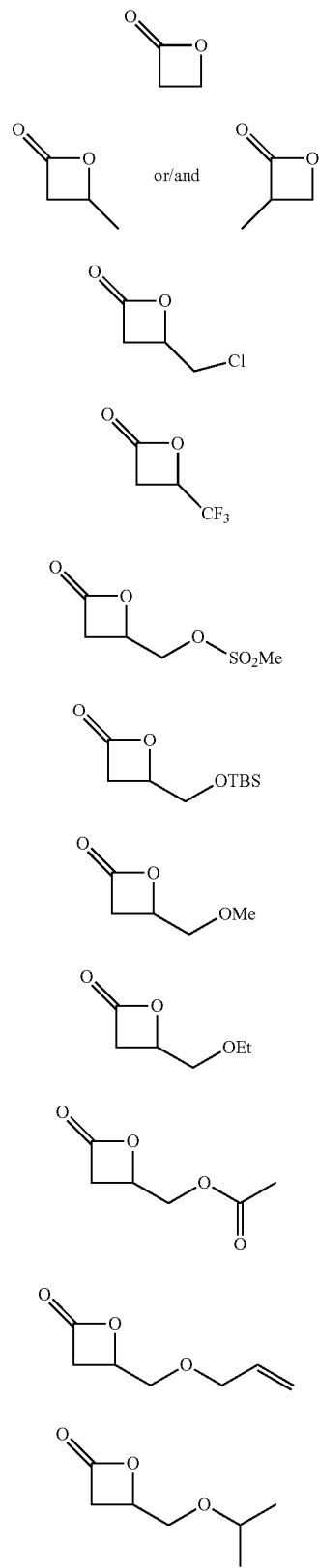

TABLE 1-continued
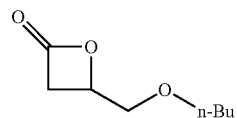
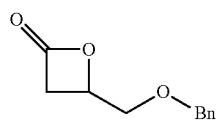 [SMILES: O=C1CC(COCc2ccccc2)O1]
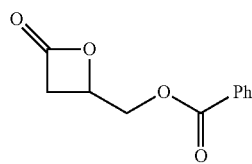 [SMILES: O=C1CC(COC(=O)c2ccccc2)O1]
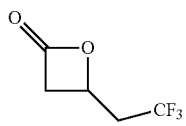
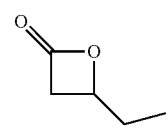
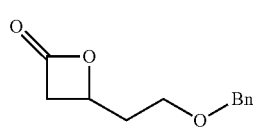 [SMILES: O=C1CC(CCOCc2ccccc2)O1]
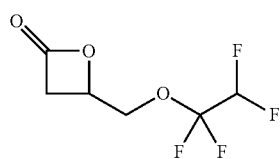 [SMILES: O=C1CC(COC(F)(F)C(F)F)O1]
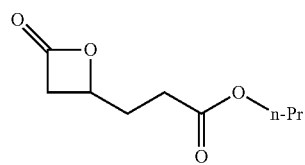
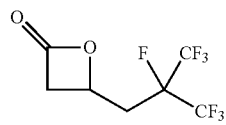
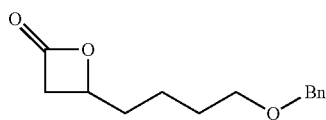 [SMILES: O=C1CC(CCCCOCc2ccccc2)O1]
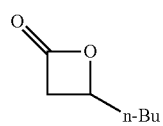

TABLE 1-continued
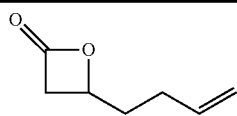
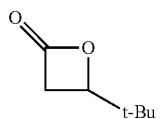
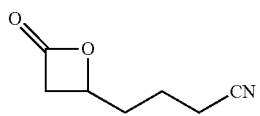
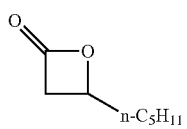
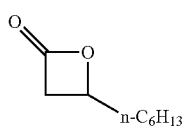
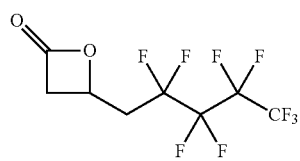 [SMILES: O=C1CC(CC(F)(F)C(F)(F)C(F)(F)C(F)(F)F)O1]
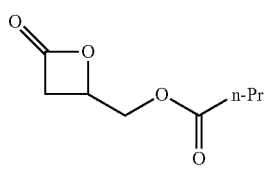
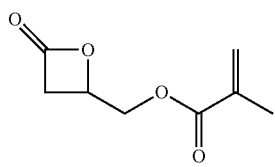
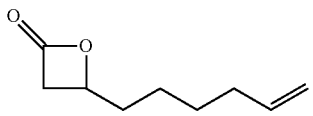
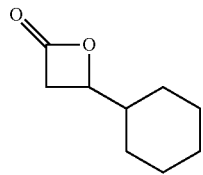 [SMILES: O=C1CC(C2CCCCC2)O1]
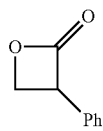

TABLE 1-continued
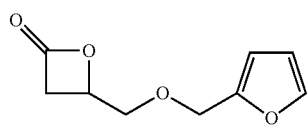 [SMILES: O=C1CC(COCc2ccco2)O1]
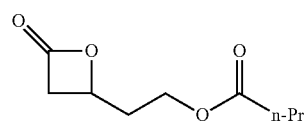
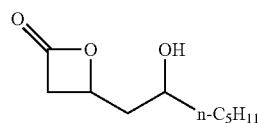
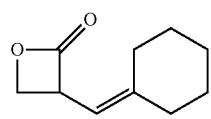
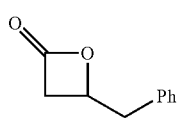 [SMILES: O=C1CC(Cc2ccccc2)O1]
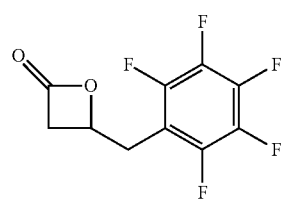 [SMILES: O=C1CC(Cc2c(F)c(F)c(F)c(F)c2F)O1]
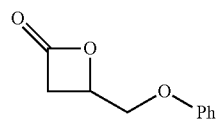
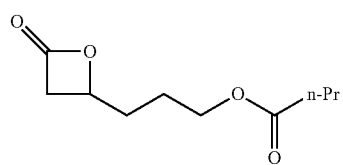
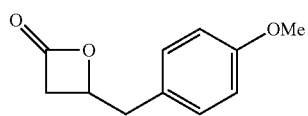 [SMILES: COc1ccc(CC2CC(=O)O2)cc1]
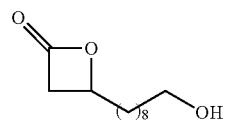
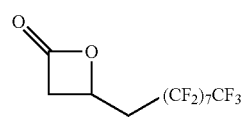

TABLE 1-continued
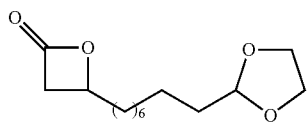
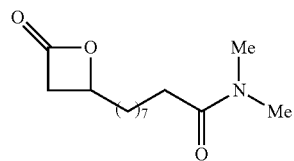
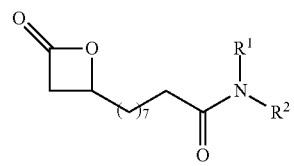
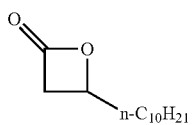
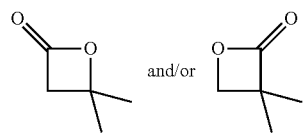
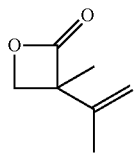
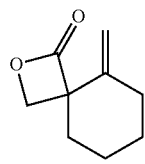
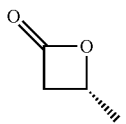
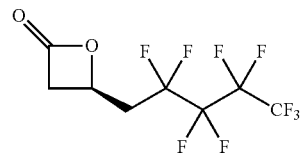 [SMILES: O=C1C[C@H](CC(F)(F)C(F)(F)C(F)(F)C(F)(F)F)O1]
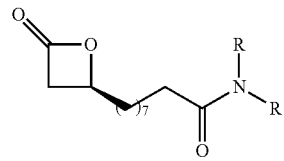

TABLE 1-continued
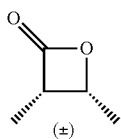
(±)
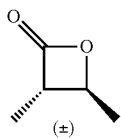
(±)
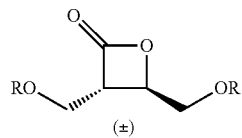
(±)
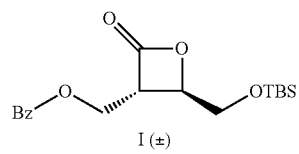
I (±)
and/or
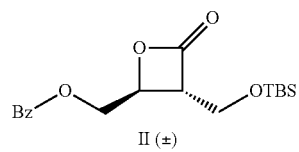
II (±)
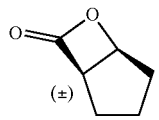
(±)
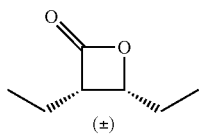
(±)
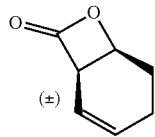
(±)
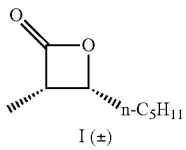
I (±)
and/or
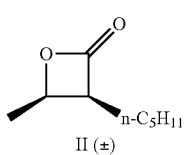
II (±)

TABLE 1-continued
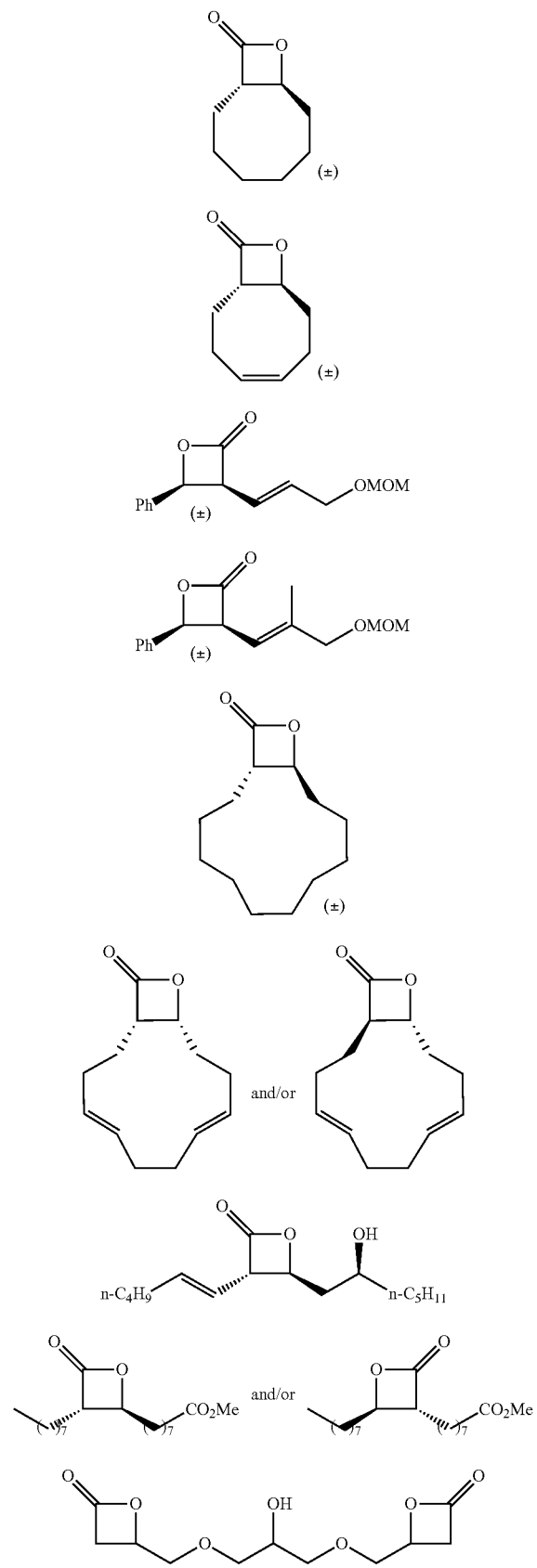

TABLE 1-continued

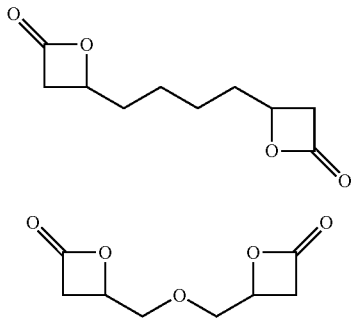

In certain preferred embodiments, the processes of the present invention may produce an organic acid product directly from a beta-lactone intermediate with a heterogenous catalyst. Such processes may produce organic acid products in high yields, by minimizing other by-products that may form, such as polylactones and polyorganic acids. Such methods produce at least one organic acid product from at least one beta-lactone reagent in a single step reaction.

The reactor systems and processes for producing an organic acid product from a beta-lactone reagent use a heterogeneous catalyst such as zeolite, metal oxide, supported acid such as phosphoric acid (solid phosphoric acid—SPA), and/or heteropolyacid. In certain preferred embodiments, the at least one heterogeneous catalyst comprises silica-alumina molecular sieves, particularly those modified with phosphate compounds. Catalysts of the type that are specifically suited for this invention include alkaline-earth phosphates, supported phosphate salts, calcium hydroxyapatites, inorganic salts, metal oxides, and zeolites. In preferred embodiments, the at least one heterogeneous catalyst is an alumina-silicate molecular sieve and more preferably a zeolite having Lewis or Brönsted acidity. The zeolites can be in hydrogen form or in cation exchanged form. Suitable cations are alkali metals such as Na+ or K+; alkali-earth cations such as Ca2+, Mg2+, Sr2+, or Ba2+; Zn2+, Cu+, and Cu2+.

In certain other preferred embodiments, the processes of the present invention include a step 117 for polymerizing the beta-lactone intermediate with a polymerization initiator in the presence of at least one metal cation in at least one reaction vessel to produce a polylactone product. In certain preferred embodiments of this invention, the polymerization initiator is an ionic initiator having the general formula of M"X where M" is cationic and X is anionic. The M" is selected from the group consisting of Li+, Na+, K+, Mg2+, Ca2+, and Al3+. In some embodiments, M" is Na+. In some embodiments, M" is an organic cation. In some embodiments, the organic cation is selected from the group consisting of quaternary ammonium, imidazolium, and bis(triphenylphosphine)iminium. In some embodiments, the quaternary ammonium cation is tetraalkyl ammonium.

The X is a nucleophilic anion such as, but not limited to, compounds comprising at least one carbonxylate group, at least one alkoxide group, at least one phenoxide group, and combination thereof. In some embodiments, the nucleophilic anion is selected from the group consisting of halides, hydroxide, alkoxide, carboxylate, and combination thereof. In some embodiments, the ionic initiator is sodium acrylate. In some embodiments, the ionic initiator is tetrabutylammonium acrylate. The suitable anionic nuclephiles include $R^xO^-$, $R^xC(\!=\!O)O^-$, $R^xS^-$, $R^xO(C\!=\!O)O^-$, halide (e.g., $Br^-$, $I^-$, $Cl^-$), $R^x(SO_2)$ $O^-$ and $PR^x_3O^-$, wherein each $R^x$ is, independently, selected from hydrogen, optionally substituted aliphatic, optionally substituted heteroaliphatic, optionally substituted aryl and optionally substituted heteroaryl. In certain embodiments where the anionic nucleophile is $R^xC(\!=\!O)O^-$, $R^x$ is selected from optionally substituted aliphatic, fluorinated aliphatic, optionally substituted heteroaliphatic, optionally substituted aryl, fluorinated aryl, and optionally substituted heteroaryl. For example in certain aspects the initiator may be $CH_2\!=\!CHCO_2^-$, $CH_3CO_2^-$, or $CF_3CO_2^-$.

In certain embodiments, the homogeneous polymerization initiator is a quaternary ammonium salt (for example, tetrabutylammonium (TBA) acrylate, TBA acetate, trimethylphenylammonium acrylate, or trimethylphenylammonium acetate) or a phosphine (for example, tetraphenyl phosphonium acrylate). In some aspects, the catalyst is tetrabutylammonium acrylate, sodium acrylate, potassium acrylate, iron chloride, tetrabutylammonium acetate, trimethylphenylammonium acrylate, trimethylphenylammonium acetate, or tetraphenyl phosphonium acrylate.

The polymerization process may further comprise a polymerization initiator including but not limited to amines, polyamines, phosphines amongst others. Further, a variety of polymerization initiators may be used in the polymerization process, including by not limited to carbonates of alkali- and alkaline earth metals. In certain aspects, suitable polymerization initiators include carboxylate salts of metal ions or organic cations. In certain aspects, a polymerization initiator is combined with the production stream containing the beta-lactone intermediates. In certain aspects, the molar ratio of the polymerization initiator to the beta-lactone intermediates is about 1:15000. In certain aspects, the molar ratio of polymerization intiator:beta-lactone intermediates is about 1:100, 1:10000, 1:1000, 1:20000 or a range including any two of these ratios.

The polymerization initiator may comprise a carboxylate salt, the carboxylate has a structure such that upon initiating polymerization of the beta-lactone intermediate, the polylactone chains produced have an acrylate chain end. In certain aspects, the carboxylate ion on a polymerization initiator is the anionic form of a chain transfer agent used in the polymerization process.

In certain embodiments, steps for polymerizing the beta-lactone intermediate may be performed in the presence of a solvent. Suitable solvents for the polymerization with cyclic anhydride monomers include methylene chloride, chloroform, tetrahydrofuran, sulfolane, N-methyl pyrrolidone, diglyme, triglyme, tetraglyme, and dibasic esters.

In some embodiments, suitable catalysts, initiators, and solvent for the polymerization of the beta-lactone monomers can be found in U.S. Ser. No. 15/197,838 filed Jun. 30, 2016 the contents of which is herein incorporated by reference in its entirety. Other Catalysts suitable for the ring-opening polymerization step of the processes disclosed herein are disclosed, for example, in: Journal of the American Chemical Society (2002), 124(51), 15239-15248 Macromolecules, vol. 24, No. 20, pp. 5732-5733, Journal of Polymer Science, Part A-1, vol. 9, No. 10, pp. 2775-2787; Inoue, S., Y. Tomoi, T. Tsuruta & J. Furukawa; Macromolecules, vol. 26, No. 20, pp. 5533-5534; Macromolecules, vol. 23, No. 13, pp. 3206-3212; Polymer Preprints (1999), 40(1), 508-509; Macromolecules, vol. 21, No. 9, pp. 2657-2668; and Journal of Organometallic Chemistry, vol. 341, No. 1-3, pp. 83-9; and in U.S. Pat. Nos. 3,678,069, 3,169,945, 6,133,402; 5,648,452; 6,316,590; 6,538,101; and 6,608,170. The entirety of each of which is hereby incorporated herein by reference.

In preferred embodiments, the processes of the present invention include a step for heating the polylactone product under thermolysis conditions to produce an organic acid product in the at least one reaction vessel defining a thermolysis section. Under thermolysis conditions, the polylactone product can generally be converted to an organic acid according to the following scheme:

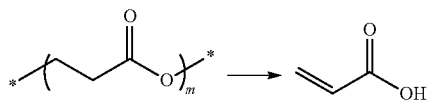

In certain embodiments, the polylactone product may undergo thermolysis continuously (e.g. in a fed batch reactor or other continuous flow reactor format). In certain embodiments, the continuous thermolysis process is linked to a continuous polymerization process to produce the organic acid product at a rate matched to the consumption rate of the at least one reaction vessel.

In certain preferred embodiments of the present invention, the processes include a step for heating the polylactone product under thermolysis conditions to an organic acid product which may favor β-elimination to produce an unsaturated alkenoic acid. Certain exemplary thermolysis reactions are shown below as non-limiting examples:

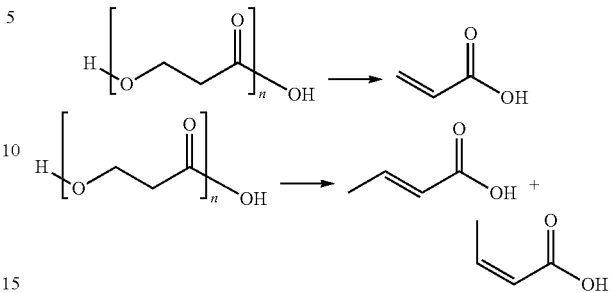

In certain embodiments of the present invention, the epoxide reagent may be a diepoxide, for example, 1,2-butadiene diepoxide. Certain exemplary reactions for producing an organic acid product from a diepoxide are shown below as non-limiting examples:

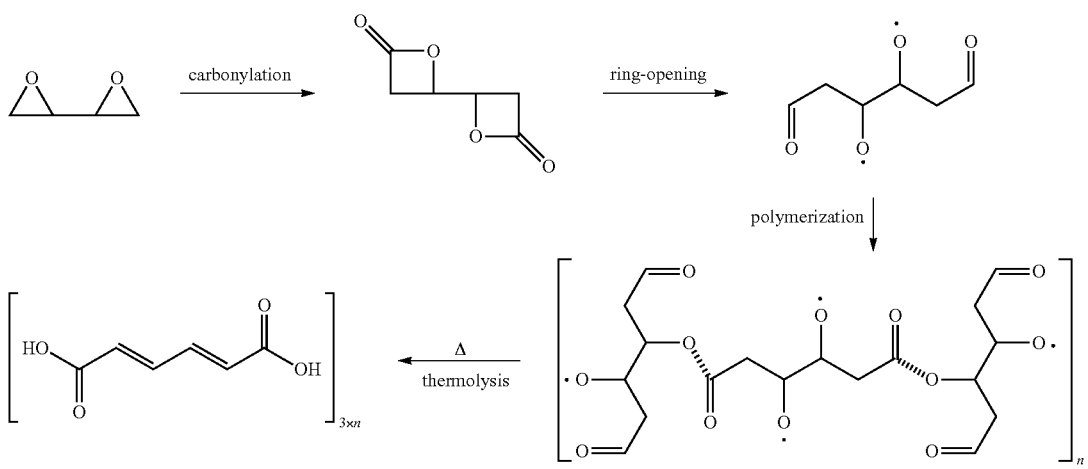

In certain preferred embodiments, the processes of the present invention include a step 119 for reacting the organic acid product with an ammonia reagent under ammoxidation conditions in at least one reaction vessel to produce an acrylonitrile product. Conditions for an ammoxidation reaction are well known in the prior art as evidenced by U.S. Pat. Nos. 5,093,299; 4,863,891; 4,767,878 and 4,503,001; herein incorporated by reference. In the step for ammoxidation of the organic acid product, the one organic acid product is reacted with an ammonia reagent. The molar ratio of the ammonia reagent to the organic acid product in the reaction may be in the range of 0.5:1 to 2:1. More preferably, the ratio may be in the range of 0.9:1 to 1.3:1.

In preferred embodiments, ammoxidation of the organic acid product with the ammonia reagent may proceed in the presence of a catalyst. In certain preferred embodiments, the catalysts useful for ammoxidation of the one or more organic acid products may include metal and/or metal oxides including the group Cr, Al, V, Mn, Fe, Mo, Sn, Bi, and U. In some embodiments, catalysts may be supported such as on silica in order to decrease the expensive metal content of the catalyst. Certain examples of catalysts useful for ammoxidation of the one or more organic acid products include Cr2O3/Al2O3, KNaMoP/Al2O3, NaMo/Al2O3, AsFeO, SbSnO, FeBiPO, BiMoO, MoO3, MoO3/SiO2, and NaMo/Al2O3.

In some embodiments, the processes of the present invention may include a step for esterification of the organic acid product prior to a step for ammoxidation. The step for esterification includes introducing an alcohol reagent and an acid catalyst to the organic acid product through at least one feed stream inlet of the at least one reaction vessel. In certain embodiments, the step for esterification includes introducing heat the one or more reaction vessels.

Figure 2:
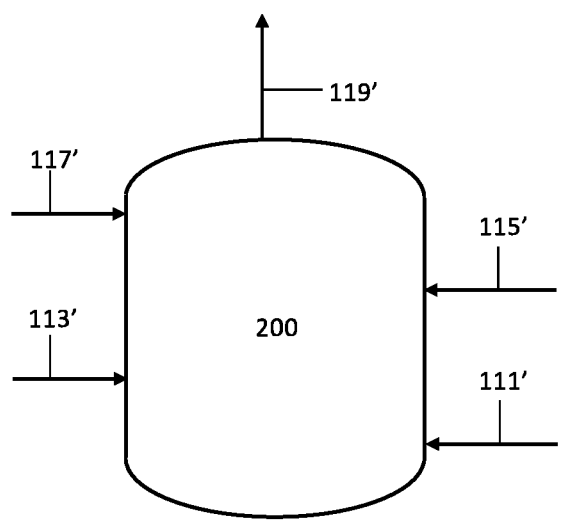
FIG. 2 is a schematic process flow diagram illustrating steps of the process flow from FIG. 1.

FIG. 2 provides a schematic diagram of some of the process steps of FIG. 1. The process flow of FIG. 2 is configured for production of an organic acid product in a reaction vessel 200. An epoxide reagent and carbon monoxide reagent is introduced through a feed stream inlet 111' defined by the reaction vessel 200. The epoxide reagent and carbon monoxide reagent are contacted with at a carbonylation catalyst to produce a beta-lactone intermediate such as by directing the carbonylation catalyst through a feed stream inlet 113' defined by the reaction vessel 200. The beta-lactone intermediate is polymerized to produce a polylactone product such as by directing a polymerization initiator in the presence of a metal cation through a feed stream inlet 115' defined by the reaction vessel. Heat is introduced to the reaction vessel 200 such as by a heating baffle for heating the polylactone product under thermolysis conditions to produce an unsaturated organic acid product 117'. In the reaction vessel 200, the unsaturated organic acid product is reacted with an ammonia reagent in the presence of a catalyst to produce an acrylonitrile product 119'.

Figure 3:
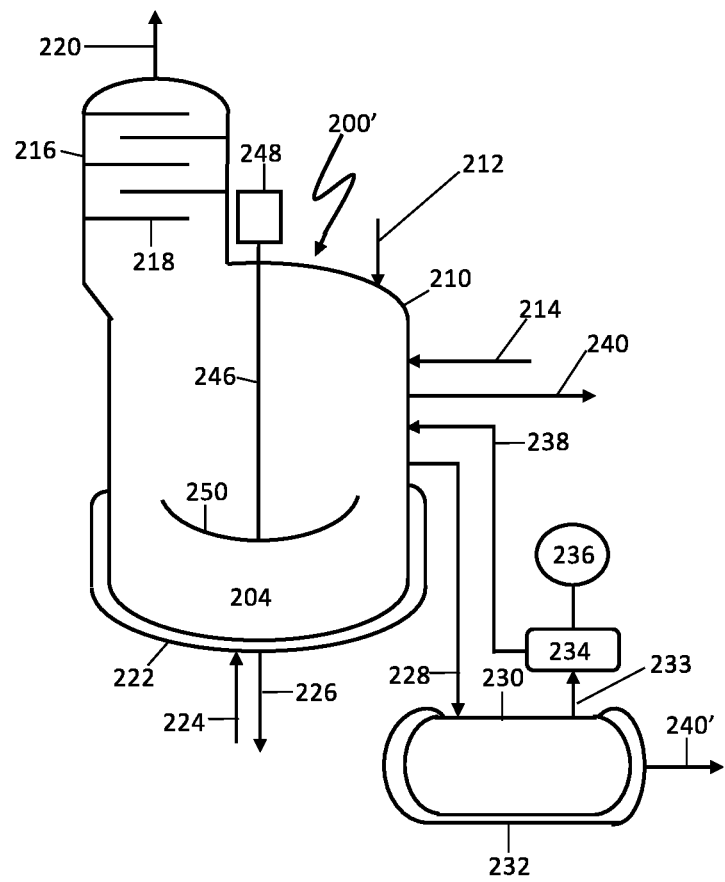
FIG. 3 schematically illustrates a preferred reaction vessel and related equipment in a process flow diagram for production of an acrylonitrile product.

FIG. 3 illustrates a preferred embodiment of a reaction vessel 200' configured for thermolysis. In the FIG. 3 illustrated embodiment, the reaction vessel 200' includes a thermolysis section 210 adapted for receiving a feed stream comprising a polylactone product and a retaining volume 204 in a lower portion of the thermolysis section adapted for retaining the polylactone product. The feed stream comprising the polylactone product may be passed to the thermolysis section 210 by a feed stream inlet 212 defined by the reaction vessel 200'. In some embodiments, a polymerization inhibitor may be directly introduced to the thermolysis section 210 by an additive stream inlet 214 defined by the reaction vessel 200'. Additionally, oligomers of a variety of chain lengths, residual polymerization initiator, polymerization inhibitor, impurities, and/or other unwanted materials may be removed directly from the thermolysis section 210 by a purge stream outlet 240 defined by the reaction vessel 200'.

In certain preferred embodiments of the present invention, the apparatus includes a reaction vessel 200' defining a separation section 216 configured for direct communication with an upper portion of the reaction vessel 200'. The separation section 216 may comprise a fractionation column having one or more trays 218. A product stream comprising an organic acid product is withdrawn from a product stream outlet 220 defined by an upper portion of the reaction vessel 200 including the separation section 216. A portion of product stream may be cooled and returned to the one or more trays 218 of the separation section 216. A condensate may flow out of the bottom of the separation section 216 and return comprising a mixture of polylactone oligomers to the thermolysis section 210 for a thermolysis reaction. The product stream comprising the organic acid product may undergo cooling and further processing. The processing may include additional purification to remove by-products, unrelated feed components and other impurities.

The reaction vessel 200' also includes a heater 222 for endothermic conversion of the polylactone product to the organic acid product. FIG. 3 shows a heater 222 in the form of a heating jacket that surrounds a lower portion of the thermolysis section 210. In alternate embodiments, the heater 222 may be an external heat exchanger connected to the thermolysis section 210 of the reaction vessel 200' including a pump-around loop for circulation of hot fluid. In the embodiment of FIG. 3, a hot fluid stream influent line 224 delivers hot fluid to the heater 222 and a hot fluid stream effluent line 226 removes hot fluid from the heater 222. Suitable fluids include hot oil and molten salts.

In certain preferred embodiments, the reaction vessel 200' may define a slip stream outlet 228 which may direct polylactone oligomers of a variety of chain lengths, residual polymerization initiator, radical polymerization inhibitor, and/or radically polymerized organic acid of a variety of chain lengths to a bottoms squeezer 230. The bottoms squeezer 230 is a reactive distillation vessel such as a thin film evaporator for thermolysis of polylactone oligomers into volatile species like the organic acid product and polylactone oligomers of a variety of chain lengths. The bottoms squeezer 230 is connected to a bottoms squeezer heater 232 for heating the contents of the bottoms squeezer 230. The bottoms squeezer 230 defines an outlet 233 by which volatile species pass to a bottoms squeezer condenser 234 by a vacuum source 236. Condensate from the bottoms squeezer 230 is returned to the thermolysis section 210 and/or mixed with the product stream from the product stream outlet 220. The volatile species like the organic acid product are returned to the thermolysis section 210 by a recycle stream inlet 238. The liquid residence time in the bottoms squeezer 230 may be between 5 seconds and 3 hours, depending upon flow conditions and operating temperature, but is preferably 10-30 minutes. Less volatile and non-decomposable species such as residual polymerization initiator, radical polymerization inhibitor, and radically polymerized polyorganic acid are removed from the bottoms squeezer by a purge stream outlet 240'. Additionally, polylactone oligomers of a variety of chain lengths, residual polymerization initiator, radical polymerization inhibitor, and/or radically polymerized polyorganic acid, such as polyacrylic acid, of a variety of chain lengths may be removed directly from the reaction vessel 200' by a purge stream outlet 240'.

The reaction vessel 200' illustrated in FIG. 3 is configured to included mechanical mixing. A mechanical mixer 246 may be rotated by a motor 248 so that at least one blade 250 provides mechanical mixing to the material in the retaining volume 204 of the thermolysis section 210.

Figure 4:
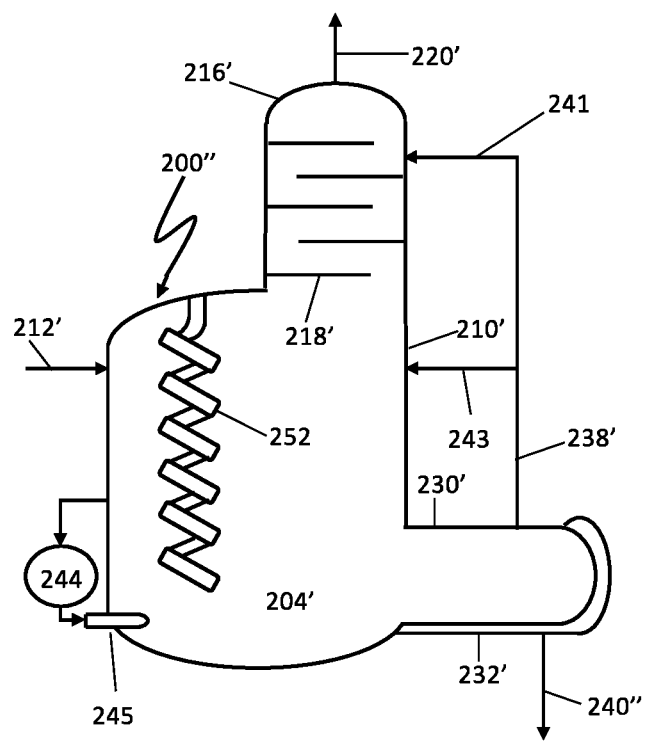
FIG. 4 illustrates another preferred embodiment including a reaction vessel for performing the processes of the present invention.

FIG. 4 illustrates another preferred embodiment of a reaction vessel 200" configured for continuous flow. The reaction vessel 200" includes a thermolysis section 210 and defines a feed stream inlet 212' for receiving a feed stream comprising a polylactone product. The thermolysis section 210' is in direct communication with a separation section 216' connected to a product stream outlet 220' at the top of the separation section 216'. The separation section 216' is a rectification column with one or more trays 218'. In FIG. 4, a heating coil 252 has heat exchange tubes through which hot liquid or gas may be circulated for providing heat internally to the feed stream. The retaining volume 204' of the thermolysis section 210' is also in direct communication with a bottoms squeezer 230' so that polylactone oligomers of a variety of chain lengths, residual polymerization initiator, radical polymerization inhibitor, and/or radically polymerized polyorganic acid of a variety of chain lengths may be heated under thermolysis conditions. The bottoms squeezer 230' is connected to a bottoms squeezer heater 232' for thermolyzing small chain polylactone oligomers and distilling the organic acid product to be returned to the separation section 216. A recycle stream inlet 238' delivers recycled unreacted polylactone and/or organic acid product to recycle stream inlets 241 and 243. Less volatile materials such as residual polymerization initiator, radical polymerization inhibitor, and/or radically polymerized polyorganic acid of a variety of chain lengths may be removed by a purge stream line 240'. The contents of the thermolysis section 210' are mixed by a jet mixer 245 which may remove liquid from the retaining volume 204' of the thermolysis section 210' and return the liquid to the retaining volume 204' of the thermolysis section 210' such as with a pump 244.

In certain embodiments, such as the embodiment illustrated in FIG. 4, it may be preferable to withdraw the product stream comprising an organic acid product in a vapor phase. The separation section 216 illustrated in FIG. 4 may cause the feed stream in vapor phase to undergo condensation and/or distillation to remove higher-boiling and/or lower-boiling impurities. In some embodiments, if distillation is required to remove higher-boiling impurities, then polymerization inhibitor may be introduced to any liquid phase organic acid, for example, in the thermolysis section 210' and/or the separation section 216'. In some embodiments, if 4-methoxyphenol is used as a polymerization inhibitor, the concentration of dissolved oxygen may be managed such as by introducing oxygen gas or oxygen mixed with an inert gas to the thermolysis section 210'. The bottom portions from the separation section 216' shall optimally be returned to the thermolysis section 210' for further thermolysis. In some embodiments, the separation section 216' may reduce the partial pressure of organic acid and the concentration organic acid in the reaction vessel's liquid contents. In another example, said vapors may be expelled from the product stream outlet when the partial pressure of organic acid is above a defined amount.

In some embodiments, such as the FIG. 4 illustrated embodiment, the bottoms squeezer 230' may be a reactive distillation vessel, such as a thin film evaporator either oriented vertically or horizontally, or a continuous agitated-tank reactor followed by a condenser (not shown in FIG. 4). The bottoms squeezer 230' may be operated at a temperature preferably in excess of 100° C., but may also be heated along its length to a higher temperature, cooled immediately to a lower temperature, and/or cooled along the length of the bottoms squeezer 230' to a lower temperature. The bottoms squeezer 230' may generally be operated below atmospheric pressure. The liquid residence time in the bottoms squeezer may be between 30 seconds and 30 hours, depending upon feed conditions and operating temperature, but preferably 2-15 minutes.

In certain embodiments, the residual waste stream purged from the at least one reaction vessel may include, for example, high boiling organics (or organic heavies), for example, resulting from the polymerization catalyst and succinic anhydride, as well as the cationic and anionic carbonylation catalyst species if the carbonylation catalyst was not separated prior to thermolysis. In some embodiments, the high boiling organics (or organic heavies) may include any compounds which is not the organic acid product. In certain embodiments, the high boiling organics (or organic heavies) may include any compounds which remain in a bottoms stream after condensing the organic acid product. In some embodiments, the high boiling organics (or organic heavies) may include polymerization catalyst, or carbonylation catalyst or components thereof (for example, organic compounds from the carbonylation catalyst).

In some embodiments, the at least one reaction vessel defining a thermolysis section is a fluidized bed reactor. In some embodiments, inert gas may be used to fluidize inert solid heat transfer medium and heat the polylactone product that is fed into the thermolysis section. In some embodiments, the polylactone product may be fed into the thermolysis section in molten form, for example, via a spay nozzle. In some embodiments, the molten form may help facilitate the dispersion of the one or more polylactone products inside the thermolysis section.

In some embodiments, the at least one reaction vessel defining a thermolysis section may be equipped with a cyclone that returns heat transfer medium solid back to the thermolysis section. An inert gas, one or more organic acid products, and higher boiling impurities (such as substituted succinic anhydride and/or substituted acrylic acid dimer) are fed from the cyclone to a partial condenser where impurities are separated. For example, the condenser may be used to condense the high boiling impurities, and such impurities can then be purged from the one or more reaction vessels as a residual waste stream.

In other embodiments, the one or more reaction vessels include a moving bed reactor. One or more polylactone products may be fed into the moving bed reactor as a solid and one or more organic acid products may exit the moving bed reactor as a vapor stream which may be condensed.

In certain preferred embodiments, the reactor systems and processes of the present invention may include heating the polylactone product to a temperature in a thermolysis section from about 150° C. to about 300° C. or from about 250° C. to about 300° C. In other embodiments, heating the polylactone product to a temperature in a thermolysis section may be in the range from about 300° C. to about 500° C. In some variations, operating temperature is the average temperature of the contents of the thermolysis section.

In some variations, the operating pressure in the thermolysis section is from about 0.01 atmospheres to about 500 atmospheres (absolute), from about 1 atmosphere to about 100 atmospheres (absolute), or from about 10 atmospheres to about 50 atmospheres (absolute).

In preferred embodiments, one or more polylactone product stream enters one or more reaction vessels defining a thermolysis section, either in solid or liquid phase at a temperature between 100° C. and 320° C., and absolute pressure between 1 mmHg and 5000 mmHg. In certain preferred embodiments, the reactor systems and processes of the present invention provide for heat transfer input, for example internal coils, external heat exchanger with a pump-around loop from and back to one or more reaction vessels, or a baffled jacket on the walls of the one or more reaction vessels. Alternatively, a high temperature liquid or gas that that does not significantly affect the reaction chemistry may be introduced to maintain desired reaction temperature and separated downstream. Depending upon time and temperature residence time for complete conversion may vary from a few seconds to 24 hours or more. Mixing of the contents of the reactor may also improve mass and heat transfer.

In preferred embodiments, the reactor systems and processes of the present invention may provide for thermolysis conditions and certain configurations that will minimize the loss of the one or more organic acid products. For example, the reactor systems and processes of the present invention may include the use of a depolymerization catalyst to decrease required reaction severity and/or use radical polymerization inhibitor. Advantageously, the depolymerization catalyst may be one or more salts of the one or more organic acid products.

In certain preferred embodiments, the reactor systems and processes of the present invention can minimize the concentration of the one or more organic acid products in the liquid phase, for example, by removing vapors from the headspace of the one or more reaction vessels and lowering the one or more organic acid products' partial pressure in the headspace. Sparging with an inert gas, preferably continuously will further reduce the concentration of the one or more organic acid products in the reactor's liquid contents. Withdrawal of liquid effluent stream and any other nonvolatile components may also be desired to manage accumulation of unwanted polymers. These may be directed to a second thermolysis reactor, to waste treatment, or to a reactive distillation to convert the considerable polylactone in the stream to volatile species such as one or more organic acid products. The vapor effluent from this distillation operation can flow back to the primary reactor, or be mixed with the vapor effluent from the primary reactor.

In some embodiments, the reactor systems and processes perform thermolysis under an oxygen and water free atmosphere. For example, in certain variations, the amount of oxygen present in the thermolysis reactor is less than 1 wt %, less than 0.5 wt %, less than 0.01 wt %, or less than 0.001 wt %. In certain variations, the amount of water present in the thermolysis reactor is less than 1 wt %, less than 0.5 wt %, less than 0.01 wt %, or less than 0.001 wt %.

In certain preferred embodiments, the reactor systems and processes of the present invention include configurations and steps to manage and integrate heat produced. Advantageously, heat produced during certain steps and/or in certain reaction vessels may be transferred to other steps and/or reaction vessels minimizing reliance on external heat sources. The carbonylation reaction which occurs during certain steps and the polymerization reaction which occurs during certain steps are exothermic. The heat generated from exothermic reactions, such as from a reaction vessel defining a carbonylation section and/or polymerization section, can be captured and used, such as by retaining the heat within a heat transfer medium and directing the heat transfer medium to a reaction vessel with thermolysis section. For example, in some variations of the reactor systems and processes provided herein, steam may be generated in heat transfer equipment (e.g., shell and tube heat exchanger and reactor cooling jacket) via a temperature gradient between process fluid and water/steam. In other embodiments of the reactor systems and processes provided herein, other suitable heat transfer fluids may be used.

In certain preferred embodiments, an ammoxidation reaction is performed in fluid bed reactor, a transport line reactor and/or a hybrid reactor. Certain reaction configurations include those described in U.S. Pat. No. 3,230,246, and 6,143,915 herein incorporated by reference. In certain embodiments, the one or more reaction vessels defining an ammoxidation section may be configured as a fluid bed reactor, for example, introducing solid phase ammoxidation catalyst to the ammoxidation section and passing one or more organic acid products and one or more ammonia reagents in liquid phase through the ammoxidation catalyst. In certain embodiments, the one or more reaction vessels defining an ammoxidation section may be configured as a transport line reactor, for example, the one or more organic acid products and/or one or more ammonia reagents may be circulated through the one or more reaction vessels as a gas at high temperature and high velocity. In certain embodiments, the one or more reaction vessels defining an ammoxidation section may be configured as a hybrid reactor, for example, the introducing solid phase ammoxidation catalyst and liquid phase one or more organic acid products to the ammoxidation section and circulating one or more ammonia reagents as a gas at high temperature and high velocity.

Figure 5:
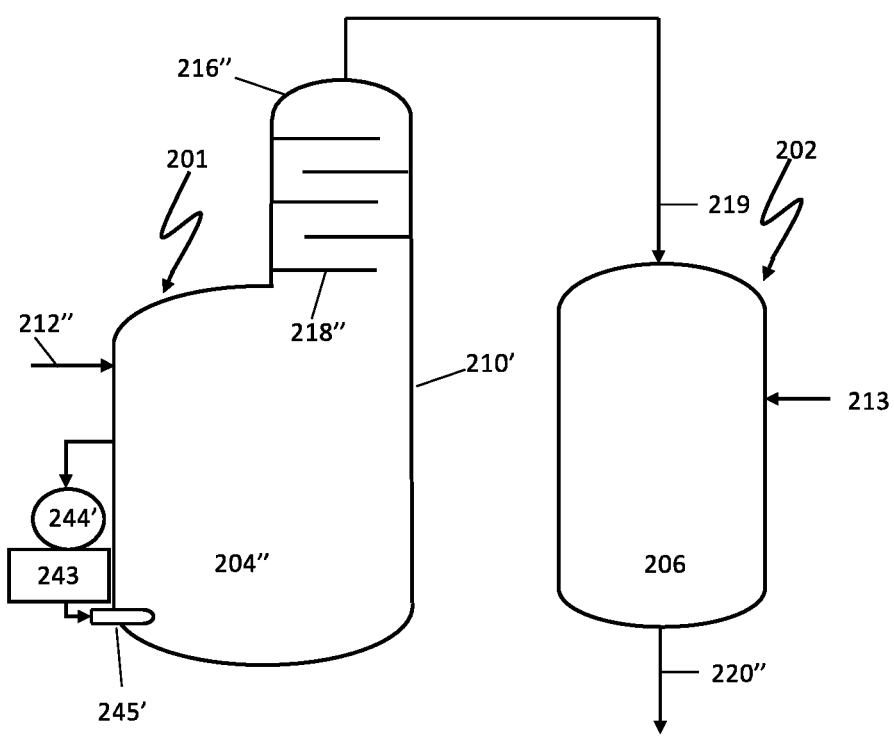
FIG. 5 illustrates another preferred embodiment of a reactor system comprising two reaction vessels for production of an acrylonitrile product.

FIG. 5 illustrates a preferred embodiment of a reactor system comprising a first reaction vessel 201 and a second reaction vessel 202. In the FIG. 5 illustrated embodiment, the first reaction vessel 201 includes a thermolysis section 210" adapted for receiving a feed stream comprising a polylactone product and a retaining volume 204" in a lower portion of the thermolysis section 210' adapted for retaining the polylactone product. The feed stream comprising the polylactone product may be passed to the thermolysis section 210 by a feed stream inlet 212" defined by the reaction vessel 201. A pump 244' directs a portion of the polylactone product from the retaining volume and through a heater 243 for a thermolysis reaction. Heated polylactone product and organic acid product is returned to the retaining volume 204" by a jetmixer 245'. The organic acid product is separated from the polylactone product by the one or more trays 218' in the separation section 216". The organic acid product is directed to the second reaction vessel 202 comprising an ammoxidation section 206 through a transfer stream inlet 219 defined by the second reaction vessel 202. The organic acid product in the ammoxidation section 206 is reacted with an ammonia reagent and catalyst introduced to the ammoxidation section 206 through a second feed stream inlet 213 defined by the second reaction vessel 202. An acrylonitrile product produced from ammoxidation is removed from the reactor system through a product stream outlet 220" defined by the second reaction vessel 202.

In some embodiments, the one or more reaction vessels defining an esterification section may be configured for refluxing the one or more organic acid products and one or more alcohols in the presence of an acid catalyst. The esterification section may be in communication with a separation section so that heated materials in the gas phase may form condensate and return to the esterification section and one or more ester products may be recovered and/or undergo ammoxidation to produce one or more acrylonitrile products.

In certain embodiments of the present invention, the components of the reactor system may be in two or more locations which are remote from each other. In some embodiments, one or more reaction vessels defining a polymerization section may be in a location remote from one or more reaction vessels defining a thermolysis section. In other embodiments, one or more reaction vessels defining a carbonylation section may be in a location remote from one or more reaction vessels defining a polymerization section which may be in a location remote from one or more reaction vessels defining a thermolysis section.

In certain embodiments, reactor systems and processes of the present invention are characterized in that the location where the one or more polylactone products are produced (i.e. the first location) and the location where at least a portion of the one or more polylactone products undergoes thermolysis to produce one or more organic acids (i.e. the second location) are at least 10 miles apart. In certain embodiments, the first location and the second location are at least 1,000 miles apart. In certain embodiments, the first location and the second location are 5,000 miles apart. In certain embodiments, the first location and the second location are in different countries. In certain embodiments, the first location and the second location are on different continents. Price differences between different locations can make it advantageous to form the one or more polylactone products at one location, and to liberate the one or more organic acid products at a different location. The ability to safely store and transport the one or more polylactone products enables the formation of the one or more polylactone products at a first location where the cost of raw materials is less than at a second location, followed by transportation to the second location and subsequent thermolysis to liberate the one or more organic acid products.

EXAMPLES

Several acronyms and abbreviations are used throughout this section. For clarity, the most commonly used are presented here. Ethylene Oxide ("EO"); Carbon Monoxide ("CO"); Propylene Oxide ("PO"); Turnover Frequency ("TOF"); Propiolactone or beta-Propiolactone ("PL:); Butyrolactone or beta-Butyrolactone ("BBL"); concentrations are indicated with brackets, e.g., concentration of Propiolactone [PL]; Freeze-Pump-Thaw ("FPT").

Examples 1-17 are disclosed in granted U.S. Pat. No. 8,445,703, herein incorporated by reference.

Example 1: Conversion of Ethylene Epoxide to β-Propiolactone

Temperature and pressure effect on carbonylation of EO was studied by varying the temperature and pressure.

TABLE 2

Temperature and pressure effect on catalyst activity in THF

| Temp rxn # | pressure (° C.) | yield (%) (psi) | $EO^c$ | $Ald.^c$ | $PL^c$ | $SA^c$ |
|---|---|---|---|---|---|---|
| $29\text{-}39^a$ | 30 | 200 | 69 | 0 | 22 | 0 |
| $29\text{-}56^b$ | 60 | 200 | 0.4 | 5 | 92 | 0.1 |
| $29\text{-}59^b$ | 30 | 600 | 44 | 0 | 44 | 0 |
| $29\text{-}54^b$ | 60 | 600 | 0 | 0 | 88 | 8 |
| $29\text{-}57^b$ | 60 | 600 | 0 | trace | 81 | 13 |
| $29\text{-}66^b$ | 45 | 400 | 25 | trace | 73 | 0 |

* Conditions: EO (1.8M; Arc), catalyst: [(ClTPP)Al][Co(CO)$_4$] (60 μmol), EO:cat = 1500:1, total volume: 50 mL (in THF), agitation speed: 730 rpm, reaction time: 3 h, and internal standard: hexamethylbenzene.
$^a$catalyst: hexamethylbenzene (0.5 mmol; Alfa Aesar (Ward Hill, MA), and THF (received from the column; FPT *2)
$^b$catalyst: hexamethylbenzene (1.0 mmol; TCI), and THF (dried over 4 Å sieves and stored in the glove box; FPT *2)
$^c$EO (ethylene oxide), Ald. (acetaldehyde), PL (propiolactone), and SA (succinic anhydride)

A pressure increase from 200 psi of CO to 600 psi at 30° C. doubled the yield of propiolactone (see 29-39 and 29-59 in Table 2). When the reaction temperature was increased from 30° C. to 60° C. at 200 psi of CO (see 29-39 and 29-54), the reaction went to completion and the yield of propiolactone more than tripled.

Reaction Procedure A—the Reaction Procedure for Carbonylation of Ethylene Oxide in THF is as Follows:

TABLE 3

Reaction time and catalyst loading (30° C.; 200 psi CO)

| rxn # | time (h) | cat. (mmol) | EO/cat | yield (%) EO | Ald. | PL | SA | TOF (/h) |
|---|---|---|---|---|---|---|---|---|
| 29-39 | 3 | 0.06 | 1500 | 69 | 0 | 22 | 0 | 110 |
| 29-38 | 6 | 0.06 | 1500 | 63 | 0 | 28 | 0 | 70 |
| 29-43 | 3 | 0.12 | 750 | 60 | 0 | 32 | 0 | 80 |

* Conditions: EO (1.8M), catalyst: [(ClTPP)Al][Co(CO)$_4$] (60 μmol), EO:cat = 1500:1, total volume: 50 mL (in THF), agitation speed: 730 rpm, reaction time: 3 h, internal standard: hexamethylbenzene (0.5 mmol; Alfa Aesar), and THF (received from the column; FPT *2)

A 300 mL Parr reactor was dried overnight under vacuum. In a nitrogen glovebox, the reactor was charged with [(ClTPP)Al][Co(CO)4] (66 mg, 60 mmol), hexamethylbenzene (162 mg, 1.0 mmol), and THF (dried over 4 Å molecular sieves, and freeze, pump, and thaw 3 times), then closed and removed from the glovebox. Ethylene oxide was vacuum transferred to a transfer vessel from EO lecture bottle. The Parr reactor was cooled to −78° C. and high vacuum was applied to the reactor. The vacuum was disconnected from the reactor, and the transfer vessel was connected to the Parr reactor to allow EO to be vacuum transferred from the transfer vessel to the reactor at −78° C. The reaction mixture was warmed to ambient temperature and saturated with CO by pressurizing the reactor with CO to three fourth of the desired CO pressure (e.g. 150 psi), then heated to the desired temperature. After the temperature of reaction mixture reached the desired temperature, the reactor was pressurized to the desired pressure (e.g. 200 psi). The reaction mixture was agitated for 3 h. The reactor was cooled to <0° C. and vented. A portion of reaction mixture was sampled and analyzed by 1H NMR in CDCl3.

Example 2: Catalyst Loading

Catalyst concentration was doubled to see if the activity proportionally increases with the catalyst concentration increase (Nov29-39 and 29-43 in Table 3). The same reaction procedure as Procedure A was used except for the catalyst loading.

Example 3: Carbonylation of Ethylene Oxide in High Boiling Point Solvents

The ethylene oxide carbonylation in high boiling point solvents was studied. In the continuous flow process of propiolactone production, propiolactone will be isolated by distillation from the reaction mixture, and this process needs a high boiling point solvent. Top three candidates for the high boiling point solvent were chosen based on the results from propylene oxide carbonylation. The catalyst activities of the reactions in three high boiling point solvents are about one fifth of the catalyst activity in THF (Table 4).

TABLE 4

High boiling solvents

| rxn # | Solvent | Temp (° C.) | pressure (psi) | EO | Ald. | PL | SA |
|---|---|---|---|---|---|---|---|
| 29-56 | THF | 60 | 200 | 0.4 | 5 | 92 | 0.1 |
| 29-62 | DBE | 60 | 200 | 52 | 1.7 | 21 | 0 |
| 29-63 | Sulfolane | 60 | 200 | 41 | ? | 22 | ? |
| 29-64 | Pr. Carb. | 60 | 200 | 52 | trace | 15 | 0 |

* Conditions: EO (1.8M; Arc); catalyst: [(ClTPP)Al][Co(CO)4] (60 μmol); EO:cat = 1500:1; reaction time: 3 h; THF, DBE, sulfolane and propiocarbonate (dried over 4 Å sieves;; FPT *2); and internal standard: hexamethylbenzene (1.0 mmol; TCI).

Reaction Procedure B—the Reaction Procedure for Carbonylation of Ethylene Oxide in High Boiling Point Solvents is as Follows:

A 300 mL Parr reactor was dried overnight under vacuum. In a nitrogen glovebox, the reactor was charged with [(ClTPP)Al][Co(CO)4] (66 mg, 60 mmol), and hexamethylbenzene (162 mg, 1.0 mmol), then closed and removed from the glovebox. Solvent (DBE, sulfolane or propylene carbonate; each solvent was dried over 4 Å molecular sieves and degassed) was added via syringe under N2. Ethylene oxide was vacuum transferred to a transfer vessel from EO lecture bottle. The Parr reactor was cooled to −78° C. and high vacuum was applied to the reactor. The vacuum was disconnected from the reactor, and the transfer vessel was connected to the Parr reactor to allow EO to be vacuum transferred from the transfer vessel to the reactor at −78° C. The reaction mixture was warmed to ambient temperature and saturated with CO by pressurizing the reactor with CO to three fourth of the desired CO pressure (e.g. 150 psi), then heated to the desired temperature. After the temperature of reaction mixture reached the desired temperature, the reactor was pressurized to the desired pressure (e.g. 200 psi). The reaction mixture was agitated for 3 h. The reactor was cooled to <0° C. and vented. A portion of reaction mixture was sampled and analyzed by 1H NMR in CDCl3.

Example 4: EO Carbonylation in DBE (Design of Experiments)

The goal of DOE was to find major factors influencing the activity of the catalyst ([(ClTPP)Al(THF)2][Co(CO)4]) and to find the optimum reaction conditions for running the EO carbonylation in DBE. DBE (a mixture of dimethyl succinate, dimethyl glutarate, and dimethyl adipate) was selected as the solvent of choice because the reaction in DBE showed the highest β-propiolactone (PL) yield among the preliminary high boiling point solvent screening reactions. Statistical software, JMP® 8.0, (SAS Software, Cary, N.C.) was used to design and analyze DOE runs. The experiment design was created using a screening design. Six continuous factors ([EO], temperature, CO pressure, agitation speed, time, and EO/catalyst ratio) were chosen for the DOE (Table 5). Fractional factorial type design having the six continuous factors was created. The design required 16 runs to analyze the effects of the six factors and some 2 factor interactions. Additional 3 center point runs were included to measure the variability of the DOE runs (Table 5).

TABLE 5

DOE factors: EO carbonylation in DBE

| Exp # | Pattern | [EO] (M) | EO/cat. | Temp (° C.) | press (psi) | agitation (rpm) | time (h) |
|---|---|---|---|---|---|---|---|
| 1 | +−−−−+ | 1.8 | 500 | 50 | 200 | 500 | 4 |
| 2 | +++−−− | 1.8 | 1500 | 80 | 200 | 500 | 2 |
| 3 | 0 | 1.4 | 1000 | 65 | 400 | 750 | 3 |
| 4 | +−−++− | 1.8 | 500 | 50 | 600 | 1000 | 2 |
| 5 | −−+−++ | 1.0 | 500 | 80 | 200 | 1000 | 4 |
| 6 | 0 | 1.4 | 1000 | 65 | 400 | 750 | 3 |
| 7 | −++−−+ | 1.0 | 1500 | 80 | 200 | 500 | 4 |
| 8 | ++−+−− | 1.8 | 1500 | 50 | 600 | 500 | 2 |
| 9 | −−−−−− | 1.0 | 500 | 50 | 200 | 500 | 2 |
| 10 | −+++−− | 1.0 | 1500 | 80 | 600 | 1000 | 2 |
| 11 | ++++++ | 1.8 | 1500 | 80 | 600 | 1000 | 4 |
| 12 | +−++−+ | 1.8 | 500 | 80 | 600 | 500 | 4 |
| 13 | −−++−− | 1.0 | 500 | 80 | 600 | 500 | 2 |
| 14 | 0 | 1.4 | 1000 | 65 | 400 | 750 | 3 |
| 15 | −+−−+− | 1.0 | 1500 | 50 | 200 | 1000 | 2 |
| 16 | +−+−+− | 1.8 | 500 | 80 | 200 | 1000 | 2 |
| 17 | −+−+−+ | 1.0 | 1500 | 50 | 600 | 500 | 4 |
| 18 | −−−+++ | 1.0 | 500 | 50 | 600 | 1000 | 4 |
| 19 | ++−−++ | 1.8 | 1500 | 50 | 200 | 1000 | 4 |

* Conditions: EO: purchased from Arc, catalyst: [(ClTPP)Al][Co(CO)4], total volume: 60 mL, solvent: DBE (purchased from Aldrich; dried over 4 Å sieves; FPT *3; and stored in the glove box), internal standard: 1,4-di-tert-butylbenzene (1 mmol)

TABLE 6

DOE responses; EO carbonylation in DBE

| Exp # | Pattern | $Y_{Ald}$ (%) | $Y_{PL}$ (%) | $Y_{SA}$ (%) | $Y_{EO}$ (%) | $TOF_{PL}$ ($h^{-1}$) | $TOF_{CO}$ ($h^{-1}$) |
|---|---|---|---|---|---|---|---|
| 1 | +−−−−+ | 0.6 | 36.6 | 0 | 28.1 | 46 | 46 |
| 2 | +++−−− | 12.3 | 20.0 | 0 | 20.5 | 150 | 150 |
| 3 | 0 | 0.4 | 19.4 | 0 | 44.5 | 65 | 65 |
| 4 | +−−++− | 0 | 34.5 | 0 | 40.7 | 86 | 86 |

TABLE 6-continued

DOE responses; EO carbonylation in DBE

| Exp # | Pattern | $Y_{Ald}$ (%) | $Y_{PL}$ (%) | $Y_{SA}$ (%) | $Y_{EO}$ (%) | $TOF_{PL}$ (h$^{-1}$) | $TOF_{CO}$ (h$^{-1}$) |
|---|---|---|---|---|---|---|---|
| 5 | --+-++ | 30.3 | 0 | 54.2 | 0 | 0 | 136 |
| 6 | 0 | 0.6 | 23 | 0 | 38 | 77 | 77 |
| 7 | -++--+ | 35 | 35.5 | 0 | 0.8 | 133 | 133 |
| 8 | ++-+-- | 0 | 6.2 | 0 | 40.5 | 47 | 47 |
| 9 | ------ | 0.4 | 20 | 0 | 42.4 | 50 | 50 |
| 10 | -++++- | 2.4 | 20 | 0 | 39.2 | 150 | 150 |
| 11 | ++++++ | 3.3 | 33.2 | 0 | 27.8 | 125 | 125 |
| 12 | +-++-+ | 5.5 | 23.6 | 50.8 | 0.4? | 30 | 157 |
| 13 | --++-- | 5.4 | 0.7 | 68.8 | 0 | 2 | 346 |
| 14 | 0 | 0.4 | 23.6 | 0 | 26.5 | 79 | 79 |
| 15 | -+-+- | 0 | 5.3 | 0 | 41.8 | 40 | 40 |
| 16 | +-+-+- | 24.9 | 0 | 61.9 | 0 | 0 | 310 |
| 17 | -+-+-+ | 0 | 6.8 | 0 | 50.9 | 26 | 26 |
| 18 | ---+++ | 0 | 32.4 | 0 | 37 | 41 | 41 |
| 19 | ++--++ | 0 | 10.7 | 0 | 51.9 | 40 | 40 |

* $Y_{Ald}$: acetaldehyde yield based on $^1$H NMR integration of acetaldehyde and internal standard (di-tert-butylbenzene);
$Y_{PL}$: beta-propiolactone yield;
$Y_{SA}$: succinic anhydride yield;
$Y_{EO}$: percentage of EO left in the reaction mixture;
$TOF_{PL} = Y_{PL} * [EO]_0/(time * [cat])$; and
$TOF_{CO} = (Y_{PL} * [EO]_0 + Y_{SA} * [EO]_0)/(time * [cat])$.

Reaction Procedure C—the Reaction Procedure for Carbonylation of Ethylene Oxide in DBE is as Follows:

A 300 mL Parr reactor was dried overnight under vacuum. In a nitrogen glovebox, the reactor was charged with 1,4-di-tert-butylbenzene (190 mg, 1.0 mmol), and DBE (dried over 4 Å molecular sieves, and freeze, pump, and thaw 3 times). The shot tank which was connected to the reactor was charged with [(CITPP)Al][Co(CO)4] and 10 mL of DBE. The reactor was closed and removed from the glovebox. Ethylene oxide was vacuum transferred to a transfer vessel from EO lecture bottle. The Parr reactor was cooled to −78° C. and high vacuum was applied to the reactor. The vacuum was disconnected from the reactor, and the transfer vessel was connected to the Parr reactor to allow EO to be vacuum transferred from the transfer vessel to the reactor at −78° C. The reaction mixture was warmed to ambient temperature and the agitator was turned on. The reactor was heated to the desired temperature. After the temperature of reaction mixture reached the desired temperature, the shot tank was pressurized to three fourth of the desired CO pressure. The shot tank was open to the reactor to allow the catalyst solution to be added to the reactor. The reactor was pressurized to the desired pressure. The reaction mixture was agitated for indicated periods, and then it was cooled to −20° C. and vented. A portion of reaction mixture was sampled and analyzed by 1H NMR in CDCl3.

The responses for the DOE (Table 9) were acetaldehyde yield (%), PL yield (%), succinic anhydride (SA) yield (%), EO (%), TOFPL ((PL yield*[EO]0)/(time*[cat])) and TOFCO (CO insertion per catalyst per hour).

Example 6: EO Carbonylation in Sulfolane at 80° C.

EO carbonylation in sulfolane was conducted at 80° C. to compare the reaction result with the carbonylations in DBE at 80° C. (Table 7). The reaction was run at the same reaction conditions as DOE run #13. Although, the CO insertion rate (TOFCO) seems to be slower than that of DOE run #13, high PL yield and TOFPL suggests that sulfolane is the better solvent for ethylene oxide carbonylation.

TABLE 7

| [EO] (M) | EO/cat | temp (° C.) | Press (psi) | agitate (rpm) | time (h) | $Y_{Ald}$ (%) | $Y_{PL}$ (%) | $Y_{SA}$ (%) | $Y_{EO}$ (%) | $TOF_{PL}$ (h$^{-1}$) |
|---|---|---|---|---|---|---|---|---|---|---|
| 1.0 | 500 | 80 | 600 | 500 | 2 | 2.4 | 80.4 | 0 | 1.1 | 201 |

* Conditions: EO: purchased from Arc, catalyst: [(CITPP)Al][Co(CO)4], total volume: 60 mL, solvent: sulfolane (purchased from Aldrich; dried over 4 Å sieves; FPT *3), internal standard: 1,4-di-tert-butylbenzene (1 mmol), the same reaction procedure as DOE runs.

The same reaction procedure as Procedure C was used except for the solvent. Sulfolane was purchased from Aldrich, dried over 4 Å sieves and FPT*3.

Example 7: Screening [(salph)M][Co(CO)4] Catalysts

Catalysts having the structures shown in Formulas IV & V, were screened as catalyst candidate for EO carbonylation. While [(salph)Cr][Co(CO)4] showed more than twice the activity of [(CITPP)Al][Co(CO)4], [(salph)Al][Co(CO)4] showed much lower activity compared to [(salph)Cr][Co(CO)4] (Table 11). The NMR analysis of the catalyst showed that the catalyst batch contains impurities.

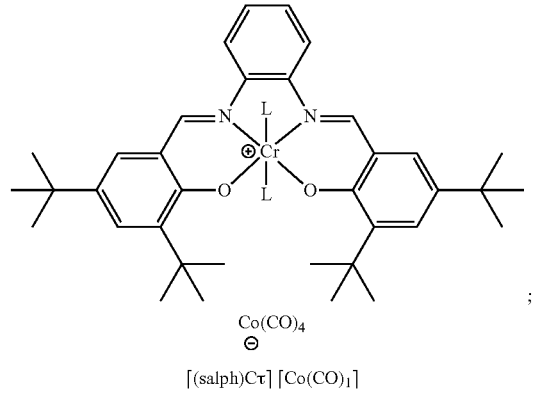

Formulas IV & V

[(salph)Cr] [Co(CO)₁]

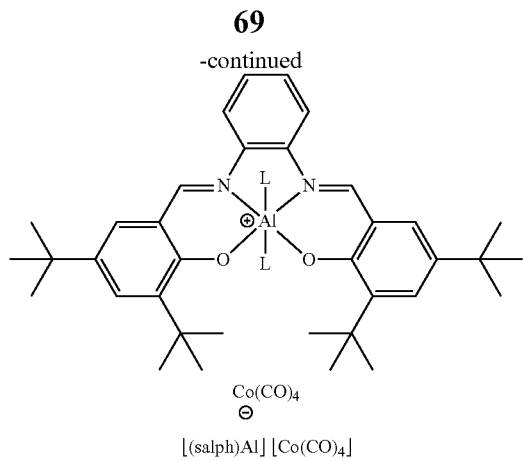

[(salph)Al] [Co(CO)₄]

L = THF

TABLE 8

| Exp. # | catalyst | EO/cat | temp (° C.) | press (psi) | $Y_{Ald}$ (%) | $Y_{PL}$ (%) | $Y_{SA}$ (%) | $Y_{EO}$ (%) | $T_{OF}$ (h⁻¹) |
|---|---|---|---|---|---|---|---|---|---|
| 29-85 | ClTPPAl[a] | 1000 | 65 | 400 | 0.6 | 23 | 0 | 38 | 77 |
| 29-102 | salphCr[b] | 1000 | 65 | 400 | 1.4 | 55.1 | 0 | 21 | 184 |
| 29-104 | salphAl[c] | 1000 | 65 | 400 | 0 | 3.5 | 0 | 44.1 | 12 |

[a]ClTPPAl = [(ClTPP)Al][Co(CO)₄]
[b]salphCr = [(salph)Cr][Co(CO)₄]
[c]salphAl = [(salph)Al][Co(CO)₄]
* Conditions: EO: purchased from Arc, [EO] = 1.4M, total volume: 60 mL, solvent: DBE (purchased from Aldrich; dried over 4 Å sieves; FPT *3), internal standard: 1,4-di-tert-butylbenzene (1 mmol), the same reaction procedure as DOE runs The same reaction procedure as Procedure C was used except for the catalyst.

Example 8: React-IR Experiments in DBE and Sulfolane

A react-IR probe was used to monitor EO carbonylations in DBE and sulfolane. Two reactions in sulfolane were monitored by react-IR (Nov29-105 and Nov29-108; Table 9). Absorbance of PL (1823 cm-1), EO (867 cm-1), and acetaldehyde (1724 cm-1) was monitored during the reactions.

TABLE 9

| Exp. # | [EO] (M) | EO/cat | Temp (° C.) | press (psi) | agitate (rpm) | $Y_{Ald}$ (%) | $Y_{PL}$ (%) | $Y_{SA}$ (%) | $Y_{EO}$ (%) |
|---|---|---|---|---|---|---|---|---|---|
| 29-105 | 1.0 | 500 | 80 | 600 | 500 | 3.8 | 53.6 | 0 | 1.4 |
| 29-108 | 1.8 | 500 | 80 | 600 | 500 | 7.9 | 46.8 | 0 | 3.2 |

* Conditions: EO: purchased from Arc, catalyst: [(ClTPP)Al][Co(CO)₄] total volume: 108 mL, solvent: sulfolane (purchased from Aldrich; dried over 4 Å sieves; FPT *3), internal standard: 1,4-di-tert-butylbenzene (1 mmol)

Reaction Procedure D—the Reaction Procedure for Carbonylation of Ethylene Oxide in DBE Monitored by React-IR is as Follows:

In a nitrogen glovebox, a 300 mL Parr reactor equipped with IR sentinel probe was charged with 1,4-di-tert-butylbenzene (190 mg, 1.0 mmol). The reactor was closed and removed from the glovebox. The IR sentinel probe was connected to a react IR (Mettler-Toledo, Columbus, Ohio). Sulfolane (dried over 4 Å molecular sieves, and degassed) was added to the reactor via syringe under N2. Ethylene oxide was vacuum transferred to a transfer vessel from EO lecture bottle. The Parr reactor was cooled 0° C. and high vacuum was applied to the reactor. The vacuum was disconnected from the reactor, and the transfer vessel was connected to the Parr reactor to allow EO to be vacuum transferred from the transfer vessel to the reactor. The reaction mixture was warmed to ambient temperature and the agitator was turned on. A shot tank was connected to the reactor and was charged with [(ClTPP)Al][Co(CO)4] and 10 mL of sulfolane. The reactor was heated to the desired temperature. After the temperature of reaction mixture reached the desired temperature, the shot tank was pressurized to three fourth of the desired CO pressure. The shot tank was open to the reactor to allow the catalyst solution to be added to the reactor. The reactor was pressurized to the desired pressure. The reaction was monitored by react-IR.

No succinic anhydride (Table 9) was formed even long after PL formation plateaued.

The EO carbonylation in DBE was also monitored using react-IR (Table 10). The reaction procedure for this reaction was modified from the DOE experiment procedure to avoid acetaldehyde formation. The catalyst solution in DBE was pressurized to 200 psi for 40 min in a Parr reactor. The temperature was increased from room temperature to 80° C., while the reactor was pressurized to 200 psi. EO was added to a shot tank, and then the shot tank was pressurized with CO to 600 psi. EO was added to the Parr reactor by opening the valve connecting the shot tank and the Parr reactor. Despite the pre-saturation of the reaction mixture with CO, 1H NMR analysis of the sample taken after the reaction shows that acetaldehyde was produced in the reaction.

TABLE 10

| Exp. # | [EO] (M) | EO/ cat | temp (° C.) | Press (psi) | Agitate (rpm) | $Y_{Ald}$ (%) | $Y_{PL}$ (%) | $Y_{SA}$ (%) | $Y_{EO}$ (%) |
|---|---|---|---|---|---|---|---|---|---|
| 29-112 | 1.0 | 500 | 80 | 600 | 500 | 7.9 | 0 | 62.7 | 0 |

* Conditions: solvent: DBE (purchased from Aldrich; dried over 4 Å sieves; FPT *3), EO: purchased from Arc, catalyst: [(ClTPP)Al][Co(CO)$_4$], total volume: 100 mL, internal standard: 1,4-bis(trimethylsilyl)benzene (1.11 mmol).

The same reaction procedure as Procedure D was used except for the solvent.

Acetaldehyde (1724 cm-1) peak was overlapped with DBE peaks and could not be monitored. The plot shows that the 2nd carbonylation (conversion from PL to SA) undergoes much faster than 1st carbonylation (from EO to PL) in DBE.

Example 9: Effect of Initial Addition of β-Propiolactone (PL)

Externally adding PL into the reaction mixture before the start of the reaction was tested using react-IR. Using PL as a solvent or a co-solvent is an attractive idea for the commercial scale process of EO carbonylation because it can facilitate the separation of PL. However, PL itself can react with CO to produce SA. The 1.0 M PL solution in sulfolane containing the catalyst was pre-saturated with 200 psi of CO for 40 min, and then EO was added to the catalyst solution with 400 psi of

TABLE 11

| Exp. # | [EO] (M) | EO/ cat | temp (° C.) | Press (psi) | agitate (rpm) | $Y_{Ald}$ (%) | $Y_{PL}$ (%) | $Y_{SA}$ (%) | $Y_{EO}$ (%) |
|---|---|---|---|---|---|---|---|---|---|
| 29-110 | 1.8 | 500 | 80 | 400 | 500 | 9.1 | 34.5 | 0 | 5.0 |

* Conditions: EO: purchased from Arc, catalyst: [(ClTPP)Al][Co(CO)$_4$], total volume: 100 mL, solvent: sulfolane (purchased from Aldrich; dried over 4 Å sieves; degassed), PL (purchased from Aldrich; dried over 4 Å sieves; degassed), internal standard: 1,4-bis(trimethylsilyl)benzene (1.11 mmol).

Reaction Procedure E—the Reaction Procedure for Carbonylation of Ethylene Oxide in PL and Sulfolane Monitored by React-IR is as Follows:

In a nitrogen glovebox, a 300 mL Parr reactor equipped with IR sentinel probe was charged with 1,4-bis(trimethylsilyl)benzene (1.11 mmol) and [(ClTPP)Al][Co(CO)4] (0.36 mmol). The reactor was closed and removed from the glovebox. The IR sentinel probe was connected to a react IR. Sulfolane (dried over 4 Å molecular sieves, and degassed) and PL (purchased from Aldrich; dried over 4 Å sieves; FPT*3), were added to the reactor via syringe under N2. The agitator was turned on, and the reaction mixture was heated to the desired temperature. A shot tank was connected to the reactor and was charged with ethylene oxide. After the temperature of reaction mixture reached the desired temperature, the shot tank was pressurized to three fourth of the desired CO pressure. The shot tank was open to the reactor to allow EO to be added to the reactor. The reactor was pressurized to the desired pressure. The reaction was monitored by react-IR.

No formation of SA was observed in 1H NMR, which means that PL did not react with CO in the presence of the catalyst during the pre-saturation step and during the reaction (temperature was ramped up from room temperature to 80° C. for 40 min during the pre-saturation step).

Even after the pre-saturation with CO, the absorbance of acetaldehyde rose quickly when EO was added, and then slowly increased after the first steep increase.

Example 10: β-Propiolactone Concentration Effect on Catalyst Activity

To understand how catalyst behaves in high PL content, we studied effect of [PL] on catalyst activity.

β-Propiolactone Concentration Effect on Catalyst Activity in Sulfolane

PL, which was purchased from Aldrich, dried over 4 Å molecular sieves, and FPT 3 times, was used as a co-solvent to study effect of PL concentration on catalyst activity in sulfolane (Table 12). The catalyst activity was measured by react-IR

TABLE 12

| Exp. # | [PL]$_0$ (M) | PL weight % | initial rate* (M/h) |
|---|---|---|---|
| 29-128 | 0 | 0 | 1.97 |
| 29-120 | 1.1 | 6.6 | 0.93 |
| 29-119 | 2.2 | 13.3 | 0.50 |

*Conditions: EO: purchased from Arc 1.8M, catalyst: [(ClTPP)Al][Co(CO)$_4$] 0.36 mmol, solvent: sulfolane (purchased from Aldrich; dried over 4 Å sieves; degassed), agitation 500 rpm, total volume 100 mL; temp 65° C.; CO pressure 400 psi
*Procedure: EO was added with 400 psi of CO to a reaction mixture containing catalyst, sulfolane, and PL at 65° C.
*Initial rate: rate of PL formation during the first 5 min The same reaction procedure as Procedure E was used except for the amount of PL.

[PL]=2.4367 AU−0.081 (AU=Absorbance unit)

As shown in Table 12, the catalyst activity is reduced at higher [PL] and is highly dependent on [PL].

Example 11: β-Propiolactone Concentration Effect on Catalyst Activity in THF Instead of adding PL before the reaction, PL was converted from EO and accumulated to a certain level. The second batch of catalyst was added in the middle of EO carbonylation when [PL] reached at a certain level. The PL formation rate at that point was measured by react-IR. Also, THF was used as solvent to increase activity and meet the targeted PL formation rate.

By subtracting the PL formation rate right before point B from the PL formation rate right after point B, the catalyst activity at 13.8 wt % of PL (1.76 M) was obtained. Using the similar experimental procedure and calculation method, the catalyst activity at 24.5 wt % was also obtained (Table 16).

TABLE 13

PL formation rate (catalyst 1.8 mM; 65° C.; 600 psi of CO)

| Exp # | [PL] (M) | PL form rate PL wt % | (M/h) |
|---|---|---|---|
| 29-135 | 0 | 0 | 5.21 |
| 29-135 | 1.76 | 13.8 | 3.26 |
| 29-137 | 3.20 | 24.5 | 2.17 |

The absorbance unit from PL peak at 1832 cm-1 was converted to concentration using the equation shown below. A plot of [PL] versus IR absorbance unit showed that as [PL] gets close to 3 M, the relationship between IR absorbance and [PL] deviated from the linearity. Therefore, a polynomial best fit was used to obtain the conversion equation.

$$[PL]=0.5075*AU3-0.0573*AU2+2.0525*AU+0.0028 \ (AU=Absorbance \ unit)$$

Example 12: Carbonylation of Propylene Oxide

The carbonylation of propylene oxide was studied by varying temperature, CO pressure, and solvent. Propylene oxide was reacted with carbon monoxide in a 300 mL Parr reactor containing [(CITPP)Al][Co(CO)4], hexamethyl benzene (internal standard), and solvent.

TABLE 14

| solvent | temp ° C. | pressure psi | PO % | β-Butyrolactone | Acetone % |
|---|---|---|---|---|---|
| dioxane | 90 | 200 | 21 | 37 | 15[b] |
| dioxane | 30 | 200 | 60 | 34 | 0 |
| dioxane | 30 | 800 | 46 | 39 | 0 |
| THF | 30 | 200 | 49 | 43 | 0 |

TABLE 14-continued

| solvent | temp ° C. | pressure psi | PO % | β-Butyrolactone | Acetone % |
|---|---|---|---|---|---|
| THF | 55 | 200 | 0 | 97 | 0 |
| THF | 30 | 800 | 8 | 91 | 0 |

* conditions: [propylene oxide] = 90 mmol (1.8M), [(CITPP)Al][Co(CO)4] = 0.06 mmol (1.2 mM), 3 h
* no succinic anhydride was observed in these reactions.
[a] yields are based on 1H NMR integration of PO, β-butyrolactone, acetone and internal standard (hexamethylbenzene)

As shown in the table above, the higher yields of β-butyrolactone were attained in THF compared to those in 1,4-dioxane, and the highest yield was obtained from the reaction in THF at 55° C. under 200 psi of CO.

Two reactions in 1,4-dioxane under 200 psi CO pressure at 90° C. and 30° C. were monitored every hour for three hours by sampling the reaction mixture. The percentage of propiolactone in the reaction mixture at 90° C. does not increase after 1 h while that in the reaction mixture at 30° C. steadily increases over time, which suggests that the catalyst is deactivated at 90° C. during the first hour of the reaction.

A representative Reaction Procedure for Carbonylation of Propylene Oxide is as follows:

A 300 mL Parr reactor was dried overnight under vacuum. In a nitrogen glovebox, the reactor was charged with [(CITPP)Al][Co(CO)4] (66 mg, 60 μmol) and hexamethylbenzene (81 mg, 0.50 mmol), then closed and removed from the glovebox. Solvent was added via syringe under N2. The reaction mixture was saturated with CO by pressurizing the reactor with CO to about 15 psi. Propylene oxide (6.3 mL, 90 mmol) was added to the reactor via syringe. The reactor was pressurized with CO to three fourth of the desired CO pressure (e.g. 150 psi), then heated to the desired temperature. After the temperature of reaction mixture reached the desired temperature, the reactor was pressurized to the desired pressure (e.g. 200 psi). The reaction mixture was agitated for 3 h. The reactor was cooled to <0° C. and vented. A portion of reaction mixture was sampled and analyzed by 1H NMR in CDCl3.

Example 13: High Boiling Solvent—Solvent Screening

Solvents were selected for the screening process based predominately upon boiling point. For efficient separation from propiolactone (b.p.=160° C.), a 30 degree boiling point difference was sought. The initial screening included dibasic ester (DBE), N-methylpyrrolidinone (NMP), triglyme, propylene carbonate, and sulfolane. Propylene oxide was used as a model for ethylene oxide, due to ease of use.

Solvent parameters such as dielectric constant, dipole moment, donor number, and CO solubility were collected and compared to the demonstrated activity (tested in the Endeavor reactor, Table 15).

TABLE 15

High-Boiling Solvent screening

| Solvent | Boiling point (° C.) | Dielectric constant | Dipole moment | Donor number[a] (kcal/mol) | CO solubility (mM) | Activity[b] (TO/h) |
|---|---|---|---|---|---|---|
| THF | 65-57 | 7.58 | 1.6 | 20 | 21.61 | 340[b] 243[c] |
| Acetonitrile | 81-82 | 37.5 | 3.92 | 14.1 | 7.42 | 0[b] |
| DME | 85 | Low | 1.31 | 20 | 33.14 | 88[b] |
| 1,4-Dioxane | 100-102 | 2.2 | 0.4 | 14.8 | 34.20 | 100[b] |
| Toluene | 110 | 2.4 | 1.3 | ~0 | 37.78 | 3.4[b] |
| DBE | 196-225 | 7.7 | 0.5-1.2 | 17.1[d] | 20.28 | 55[c] |
| DBE-3 | 215-225 | | | 17.1[d] | 25.05 | 68[c] |

TABLE 15-continued

High-Boiling Solvent screening

| Solvent | Boiling point (° C.) | Dielectric constant | Dipole moment | Donor number[a] (kcal/mol) | CO solubility (mM) | Activity[b] (TO/h) |
|---|---|---|---|---|---|---|
| NMP | 202 | 33 | 4.1 | 27.3 | 19.22 | 0[c] |
| Triglyme | 216 | 7.53 | 2.2 | 14 | 22.53 | 6.3[c] |
| Tetraglyme | 275 | | | | 20.41 | 8[c] |
| Propylene | 240 | 64.4 | 4.94 | 15.1 | 11.13 | 24[c] |
| Sulfolane | 285 | 43.3 | 4.8 | 14.8 | 8.75 | 45[c] |
| Phenyl Ether | 259 | 3.9 | 1.47 | | 17.76 | 18[c] |
| Benzyl Ether | 298 | | 1.65 | | 14.45 | 6[c] |
| Phthalan | 192 | | | | | 73[c] |
| Propylene Oxide | 34 | | | | 48.38 | ND |
| β-Butyrolactone | ~160 | | | | 25.05 | ND |
| Tetrahydrofurfurylaceate | 194-195 (753 mmHg) | | | | | ND |

[a]Donor number is a measure of the ability to solvate cations. It is the negative enthalpy value for a 1:1 adduct formation between the Lewis base and $SbCl_5$ in dilute solution in $C_2H_4Cl_2$.
[b]Reaction conditions: Parr reactor, [PO] = 1.0M, [Cat]:[PO] = 500, 40° C., 850 psi CO.
[c]Reaction conditions: Endeavor, [PO] = 1.8M, [Cat]:[PO] = 500, 40° C., 200 psi CO.
[d]Reported value is for ethyl acetate.

Solvent Selection and Optimization:

Out of all of the solvents screened for the carbonylation of propylene oxide, dibasic ester and sulfolane were chosen to pursue further studies. Simple adjustments to reaction temperature and pressure were made, resulting in improved activity in both cases (Table 16). The catalyst showed lower activity in sulfolane in general, however increase in temperature and CO pressure significantly improved the activity. Additionally, carbonylation in a mixture of THF and sulfolane (entry 5) also showed improved activity. In all cases, carbonylation in sulfolane was highly selective, with no observable byproducts such as methylsuccinic anhydride.

TABLE 16

Carbonylation of PO in high boiling solvents

| Expt | Solvent | [PO]:[Cat] | Temperature (° C.) | Pressure (psi) | Activity (TO/h) |
|---|---|---|---|---|---|
| 1 | Sulfolane | 500 | 40 | 200 | 45 |
| 2 | Sulfolane | 500 | 60 | 200 | 132 |
| 3 | Sulfolane | 500 | 60 | 400 | 195 |
| 4 | Sulfolane | 500 | 90 | 400 | 358 |
| 5 | Sulfolane/THF | 500 | 40 | 200 | 61 |
| 6 | DBE | 500 | 40 | 200 | 84 |
| 7 | DBE | 500 | 60 | 200 | 198 |
| 8 | DBE | 500 | 60 | 400 | 279 |
| 9 | DBE | 250 | 60 | 400 | 290 |

[a]Reaction conditions: Endeavor reactor, [PO] = 1.8M, 5 mL solution volume.

Carbonylation rates in DBE were also improved by increasing the temperature and CO pressure. However, selectivity in DBE was not as high as in sulfolane. Significant amounts of methylsuccinic anhydride were formed, particularly at higher temperatures. It should be noted that the temperature control in the beginning of this reaction was difficult, reaching as high as 77° C. in the first 45 min. It appeared that lactone and anhydride formation was sequential and not simultaneous. Repetition of this experiment with better temperature control results in slower overall reaction, including slower anhydride formation. A small amount of anhydride was formed when an additional injection of propylene oxide was performed. At this point lactone formation appeared to proceed at the same rate, while the anhydride concentration remained constant, lending further support to the theory that anhydride was only formed after the vast majority of epoxide is consumed. This behavior indicates that with the right conditions it would be possible to synthesize the lactone in high yields in DBE with minimal accumulation of the anhydride.

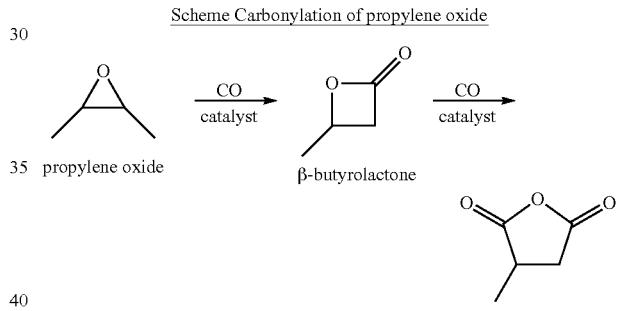

Scheme Carbonylation of propylene oxide propylene oxide → β-butyrolactone

Example 14: Catalyst Longevity

Preliminary Screening

In order to analyze the length of time the catalyst could maintain activity, a simple experiment with very low catalyst loadings ([PO]:[cat]=10,000) was performed (Table 17, entry 1). The reaction reached completion within 25 h, and samples late in the reaction suggested a linear rate of conversion with time. Carbonylation of PO under higher catalyst loadings typically give turnover frequencies (TOFs) around 500 TO/h, and even with the low catalyst loadings a TOF of 400 TO/h was obtained.

TABLE 17

Carbonylation of PO in THF at low catalyst loadings

| Entry | [PO]:[cat] | CO pressure (psi) | Time (h) | TON (mol BBL/mol cat) | % Yield |
|---|---|---|---|---|---|
| 1 | 10,000 | 200 | 25 | 10,000 | 100 |
| 2 | 20,000 | 400 | 27 | 4370 | 21.9 |
| 3 | 35,000 | 200 | 94 | 15,500 | 44.3 |
| 4 | 35,000 | 200 | 50.5 | 6,780 | 19.4 |

[a]Reaction conditions: Parr reactor, [PO] = 1.8M, 55° C., THF.

A significant deviation from linear conversion is noted at [PO]:[cat]=20,000-35,000. Possible causes for this deviation include, impurities in the solvent or substrate which may be more influential with respect to the reaction outcome at low catalyst loadings. It is also possible that the product lactone could inhibit the carbonylation reaction by competing with the epoxide for access to the catalyst. And finally, CO solubility is much lower in the lactone than in the epoxide, so as the reaction progresses, the concentration of CO could diminish.

Sequential Monomer Addition

To evaluate cyclical and/or continuous processes an experiment with a series of monomer additions was performed. The reaction was allowed to proceed to completion (3 hours), at which point another aliquot of substrate was added. This again proceeded to completion overnight, at which point yet another sample of substrate was added. This third sample only reached about 50% conversion. The reasons for this loss of activity may be similar to those listed above: impurities accumulated through successive additions of monomer, competitive product inhibition, and changing concentrations of catalyst and CO.

Example 15: Catalyst Thermal Stability

Thermo-Gravimetric Analysis ("TGA") Experiments

In order to evaluate the stability of the catalyst to potential distillation conditions, we first set out to study the thermal decomposition of the catalyst by itself. TGA was used to study the decomposition of the [(ClTPP)Al][Co(CO)4], and a decomposition resulting in about 24% mass loss starts at around 150° C. and is complete by around 210° C.

Decomposition Studies

This thermal decomposition behavior was verified by heating the material in a Schlenk tube at 200° C. for 2 days. Elemental analysis of this decomposed compound showed lower carbon and hydrogen content, and higher nitrogen and aluminum content than either the initial compound or the theoretically calculated values (Table 18). The 1H NMR spectrum showed a mixture of peaks corresponding to the known catalyst and new peaks. In addition, the material that was heated exhibited a 98% loss in catalytic activity.

TABLE 18

Carbonylation of PO in THF with thermally decomposed catalyst

| Catalyst | Purification | C (wt %) | H (wt %) | N (wt %) | Al (wt %) | TOF[a] |
|---|---|---|---|---|---|---|
| 37-019 | Precipitation | 57.21 | 3.95 | 4.82 | 2.40 | 254 |
|  | Theoretical | 61.56 | 3.69 | 5.13 | 2.47 |  |
| 26-286 | Heat at 200° C. | 51.33 | 3.38 | 5.65 | 2.71 | 4.7 |

[a]Reaction conditions: Endeavor reactor, [PO] = 1.8M, [PO]:[cat] = 500, 40° C., 400 psi, THF.

Preliminary Heat Cycles

Carrying the thermal decomposition study further, we prepared a catalyst solution in the given solvent and preheated the solution to 90° C. (a convenient temperature for vacuum distillation). The solution was then cooled, propylene oxide was added, and carbonylation carried out as usual. In the case of both THF and sulfolane, activity was comparable after a preheat period to the non-heated reaction.

TABLE 19

Carbonylation of PO with a preheat cycle

| Entry | Solvent | [PO]:[cat] | Preheat time (min) | Preheat temp (° C.) | Rxn temp (° C.) | CO pressure (psi) | Time (h) | TON (mol BBL/mol cat) | % Yield |
|---|---|---|---|---|---|---|---|---|---|
| 1 | THF | 1500 | 0 | NA | 55 | 200 | 3 | 1489 | 99 |
| 2 | THF | 1500 | 60 | 90 | 55 | 200 | 3 | 1460 | 97 |
| 3 | Sulfolane | 500 | 0 | NA | 60 | 400 | 3 | 500 | 99 |
| 4 | Sulfolane | 500 | 30 | 90 | 60 | 400 | 3 | 500 | 99 |

[a]Reaction conditions: Parr reactor, [PO] = 1.8M. For preheat cycles, the catalyst and solvent were heated under $N_2$ A. Recycle An apparatus for the distillation of lactone product directly from the Parr reactor was constructed.

Even though there is more than a 30° C. boiling point differential between the lactone and the dibasic ester solvent, this simple apparatus did not give a clean distillation. In fact more than half of the solvent in the reactor distilled with the lactone product. For this reason, sulfolane (bp=296° C.) was chosen as the solvent for the initial catalyst recycling studies (Table 20). The carbonylation conditions were held constant, at 60° C. and 400 psi CO, while the distillation temperature following the reaction was steadily increased after each cycle. Catalyst activity appears to be maintained after distillations at 90 and 100° C., but suffers markedly after distillation at 110° C.

TABLE 20

Carbonylation of PO in sulfolane with recycles.a

| Cycle | Time (h) | Turnovers (mol BBL/mol cat) | Distill time (min) | Distill temp (° C.) | Yield (g) |
|---|---|---|---|---|---|
| 1 | 1 | 90 | 30 | 90 | 5 |
| 2 | 1 | 173 | 30 | 100 | 15 |
| 3 | 1 | 102 | 30 | 110 | 7 |
| 4 | 15 | 34 | 30 | 100 | 1 | aReaction conditions: Parr reactor, [PO] = 1.8M, [PO]:[cat] = 250, 60° C., 400 psi, sulfolane.

Activity appears to be somewhat less during the second cycle, following distillation at 90 C for 35 minutes, and complete conversion was not attained. However, analysis of sulfolane solutions by NMR is greatly complicated due to the fact that our typical internal standards are insoluble in sulfolane, and the sulfolane peaks coincide with the byproduct peaks we expect.

Example 16: Catalyst Stability

Design of a continuous process for the carbonylation of ethylene oxide to form propiolactone required a catalyst which maintains activity for a significant amount of time. There were a number of factors which may influence the long-term stability of the catalyst, including temperature, solvent, impurities, and material compatibility.

Carbonylation:

The carbonylation reaction was shown in Scheme below. Coordination of an epoxide to the Lewis acid Al+ center, followed by nucleophilic attack on the epoxide by the [Co(CO)4]- anion leads to ring opening of the epoxide (2). CO insertion is typically swift to form the Co-acyl (3), which is the resting state of the catalyst in THF. Ring closing of the lactone is the rate determining step in THF, followed by loss of the lactone and coordination of another solvent molecule to reform the ion pair 1. At high temperatures and low CO concentrations, however, 2 can undergo 3-hydrogen elimination to form a ketone molecule, which is a fast and exothermic reaction. In certain solvents, the lactone can undergo subsequent carbonylation to an anhydride molecule. This typically occurs at high temperatures and when the concentration of epoxide becomes very low. The formation of anhydride is also solvent dependent, being very fast in DBE, and almost non-existent in THF and sulfolane.

R=H, Me
S=Coordinative solvent, substrate, product

Catalyst Thermal Stability

In order to assess the catalyst's thermal stability, the catalyst was heated under N2 in a Schlenk tube and the resulting material was tested for PO carbonylation activity in the Endeavor reactor (Table 21) in order to determine the importance of both temperature and time on the catalyst activity. Under the conditions of the study most of the catalyst residues maintained their activities (entries 2-5, in table 21). Only the catalysts exposed to high temperatures for long times (entries 6 and 7) resulted in a material with low activity. It appeared that the catalyst could withstand high temperatures so long as it was for less than 5 hours. 1H NMR spectroscopy of the material from entry 6 showed broad aromatic peaks and what appears to be a formula of [(ClTPP)Al][Co(CO)4](THF), where the starting catalyst (entry 1) has a formula of [(ClTPP)Al][Co(CO)4](THF)2.5 by NMR. The material produced in entry 7 unfortunately was insoluble so NMR analysis was impossible.

TABLE 21

Carbonylation of PO with catalyst that have been preheated.[a]

| Entry | Preheat temp (° C.) | Preheat time (h) | BBL equiv | PO equiv | TOF (h$^{-1}$) |
|---|---|---|---|---|---|
| 1 | NA | NA | 506 | 22 | 253 |
| 2 | 100 | 1.25 | 495 | 0 | 248 |
| 3 | 100 | 5 | 484 | 33 | 242 |
| 4 | 140 | 3.88 | 528 | 2 | 264 |
| 5 | 180 | 1.38 | 474 | 15 | 237 |

Scheme Carbonylation of epoxides with [ClTTP)Al]$^+$[Co(CO)4]$^-$

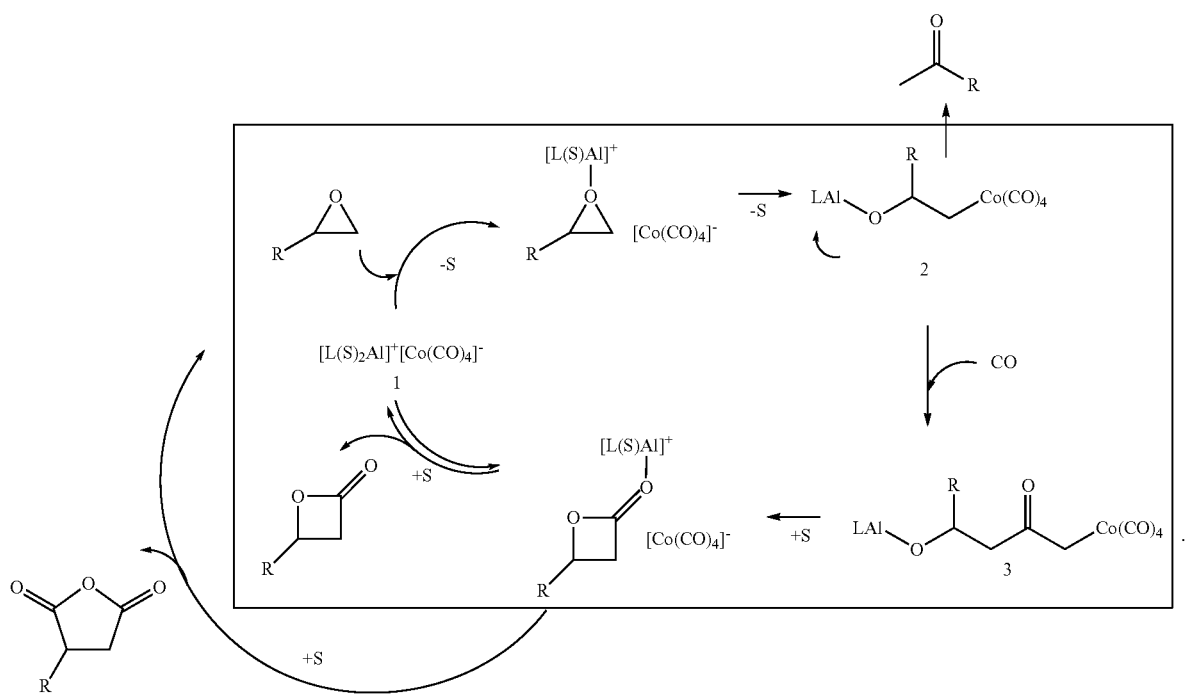

TABLE 21-continued

Carbonylation of PO with catalyst that have been preheated.[a]

| Entry | Preheat temp (° C.) | Preheat time (h) | BBL equiv | PO equiv | TOF ($h^{-1}$) |
|---|---|---|---|---|---|
| 6 | 180 | 5 | 285 | 131 | 143 |
| 7[b] | 200 | 48 | 14 | 439 | 4.7 |

[a]Catalyst heated under $N_2$ for given time at given temperature. PO carbonylation conditions: Endeavor reactor, [PO] = 1.8M, [PO]: [cat] = 500, THF 40° C., 200 psi, 2 h.
[b]Reaction time = 3 h.

Example 17: Solvent Stability

Catalyst stability in DBE-3 was evaluated by monitoring the IR spectrum of the solution under N2 for 18 h. The peak at 1887 cm-1 corresponding to the [Co(CO)4]- remained constant during that time period. PO and CO were added to the catalyst solution, and carbonylation went to completion in 2.5 h. At the end of the cycle, the [Co(CO)4]- peak returned at 79% of its original value (concentration corrections due to the addition of PO have been accounted for). However during the distillation this peak appeared to decay, and a subsequent addition of PO resulted in poor carbonylation activity.

Example 18: Conversion of β-Propiolactone to Acrylic Acid Using a Zeolite

This Example demonstrates the production of acrylic acid from bPL using a zeolite.

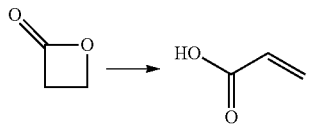

A mixture of β-propiolactone (3.0 g) and phenothiazine (9.0 mg) is added using a needle valve to a mixture of sulfolane (40.0 g) and Zeolite Y hydrogen (20.0 g) at 165° C. with 50 psi of carbon monoxide. Zeolite Y hydrogen (80:1 mole ratio SiO2/Al2O3, powder S.A. 780 m2/g) is dried under vacuum at 100° C. for one day before use. Phenothiazine is the polymerization inhibitor used. Sulfolane is the solvent used, and is dried over 3 Å molecular sieves prior to use. β-propiolactone is added slowly using the needle valve over about 8.6 minutes. The reaction mixture is heated to 170° C. to produce trans-2-butenoic acid.

The reaction is monitored by infrared spectroscopy (IR). The reaction is observed to be completed after about 3 hours, when no β-propiolactone is detectable by IR.

The zeolite is then filtered off from the reaction mixture, and a sample of the resulting mixture is dissolved in deuterium (D2O) and chloroform (CDCl3) for nuclear magnetic resonance (NMR) analysis. The observed vinyl peaks between b 5.80 and 6.47 ppm in the 1H NMR confirms the production of trans-2-butenoic acid.

Example 19: Vapor Phase Conversion of β-Propiolactone to Acrylic Acid Using a H-ZSM-5

Vapor phase conversion of β-propiolactone to acrylic acid is performed in packed-bed reactor using H-ZSM-5 (ACS Materials LLC, Si:Al=38, diameter 2 mm, surface area >=250 m2/g) as a catalyst. 11 grams of H-ZSM-5 catalyst is loaded into jacketed stainless steel 316 pipe reactor (ID 0.5 inch), the catalyst is supported between glass beads columns (stainless steel wool is placed below and above glass beads). Multi-point thermocouple is inserted through the center of the reactor and hot oil is circulated through the reactor jacket to maintain the desired reactor temperature. Propiolactone is fed to the reactor by means of saturator: N2 at the rate of 28 g/hr is flown into the bottom of the vessel containing liquid β-propiolactone at a=94° C., this results in β-propiolactone feed rate of 5 g/hr. The pressure of reactor and saturator is maintained at 9.5 psig. The reaction products are absorbed in chilled to 10° C. dichloromethane and the solution of reaction products in dichloromethane is analyzed by gas chromatography. The line between the saturator and the reactor as well as the line between the reactor and absorber are heat traced to prevent condensation of β-propiolactone to trans-2-butenoic acid. The reaction is conducted at the reactor temperature of 210° C. At these conditions, β-propiolactone conversion of greater than 99.9% is observed with selectivity of trans-2-butenoic acid product of greater than 98% (WHSV at these conditions is 0.45 h-1).

Example 20: Conversion of β-Methyl-β-Propiolactone to Trans-2-Butenoic Acid Using a Zeolite This Example demonstrates the production of trans-2-butenoic acid from β-methyl-β-propiolactone derivative using a zeolite.

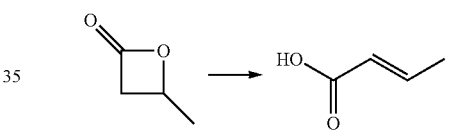

A mixture of β-methyl-β-propiolactone (3.0 g) and phenothiazine (9.0 mg) is added using a needle valve to a mixture of sulfolane (40.0 g) and Zeolite Y hydrogen (20.0 g) at 165° C. with 50 psi of carbon monoxide. Zeolite Y hydrogen (80:1 mole ratio SiO2/Al2O3, powder S.A. 780 m2/g) is dried under vacuum at 100° C. for one day before use. Phenothiazine is the polymerization inhibitor used. Sulfolane is the solvent used, and is dried over 3 Å molecular sieves prior to use. β-methyl-β-propiolactone is added slowly using the needle valve over about 8.6 minutes. The reaction mixture is heated to 170° C. to produce trans-2-butenoic acid.

The reaction is monitored by infrared spectroscopy (IR). The reaction is observed to be completed after about 3 hours, when no β-methyl-β-propiolactone is detectable by IR.

The zeolite is then filtered off from the reaction mixture, and a sample of the resulting mixture is dissolved in deuterium (D2O) and chloroform (CDCl3) for nuclear magnetic resonance (NMR) analysis. The observed vinyl peaks between b 5.80 and 6.47 ppm in the 1H NMR confirms the production of trans-2-butenoic acid.

Example 21: Vapor Phase Conversion of β-Methyl-β-Propiolactone to Trans-2-Butenoic Acid Using an H-ZSM-5

Vapor phase conversion of β-methyl-β-propiolactone to trans-2-butenoic acid is performed in packed-bed reactor using H-ZSM-5 (ACS Materials LLC, Si:Al=38, diameter 2 mm, surface area >=250 m2/g) as a catalyst. 11 grams of H-ZSM-5 catalyst is loaded into jacketed stainless steel 316 pipe reactor (ID 0.5 inch), the catalyst is supported between glass beads columns (stainless steel wool is placed below and above glass beads). Multi-point thermocouple is inserted through the center of the reactor and hot oil is circulated through the reactor jacket to maintain the desired reactor temperature. β-methyl-β-propiolactone is fed to the reactor by means of saturator: N2 at the rate of 28 g/hr is flown into the bottom of the vessel containing liquid β-methyl-β-propiolactone at a=94° C., this results in β-methyl-β-propiolactone feed rate of 5 g/hr. The pressure of reactor and saturator is maintained at 9.5 psig. The reaction products are absorbed in chilled to 10° C. dichloromethane and the solution of reaction products in dichloromethane is analyzed by gas chromatography. The line between the saturator and the reactor as well as the line between the reactor and absorber are heat traced to prevent condensation of β-methyl-β-propiolactone to trans-2-butenoic acid. The reaction is conducted at the reactor temperature of 210° C. At these conditions, β-methyl-β-propiolactone conversion of greater than 99.9% is observed with selectivity of trans-2-butenoic acid product of greater than 98% (WHSV at these conditions is 0.45 h-1).

Example 22: Conversion of 3-Methyloxetan-2-One to Methacrylic Acid Using a Zeolite This Example demonstrates the production of methacrylic acid from 3-methyloxetan-2-one using a zeolite.

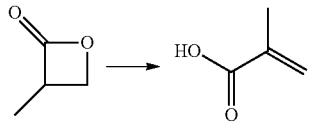

A mixture of 3-methyloxetan-2-one (3.0 g) and phenothiazine (9.0 mg) is added using a needle valve to a mixture of sulfolane (40.0 g) and Zeolite Y hydrogen (20.0 g) at 165° C. with 50 psi of carbon monoxide. Zeolite Y hydrogen (80:1 mole ratio SiO2/Al2O3, powder S.A. 780 m2/g) is dried under vacuum at 100° C. for one day before use. Phenothiazine is the polymerization inhibitor used. Sulfolane is the solvent used, and is dried over 3 Å molecular sieves prior to use. 3-methyloxetan-2-one is added slowly using the needle valve over about 8.6 minutes. The reaction mixture is heated to 170° C. to produce methacrylic acid.

The reaction is monitored by infrared spectroscopy (IR). The reaction is observed to be completed after about 3 hours, when no 3-methyloxetan-2-one is detectable by IR.

The zeolite is then filtered off from the reaction mixture, and a sample of the resulting mixture is dissolved in deuterium (D20) and chloroform (CDCl3) for nuclear magnetic resonance (NMR) analysis. The observed vinyl peaks between b 5.80 and 6.47 ppm in the 1H NMR confirms the production of methacrylic acid.

Example 4—Vapor Phase Conversion of 3-Methyloxetan-2-One to Methacrylic Acid Using an H-ZSM5

Vapor phase conversion of 3-methyloxetan-2-one to methacrylic acid is performed in packed-bed reactor using H-ZSM-5 (ACS Materials LLC, Si:Al=38, diameter 2 mm, surface area >=250 m2/g) as a catalyst. 11 grams of H-ZSM-5 catalyst is loaded into jacketed stainless steel 316 pipe reactor (ID 0.5 inch), the catalyst is supported between glass beads columns (stainless steel wool is placed below and above glass beads). Multi-point thermocouple is inserted through the center of the reactor and hot oil is circulated through the reactor jacket to maintain the desired reactor temperature. 3-methyloxetan-2-one is fed to the reactor by means of saturator: N2 at the rate of 28 g/hr is flown into the bottom of the vessel containing liquid 3-methyloxetan-2-one at a=94° C., this results in 3-methyloxetan-2-one feed rate of 5 g/hr. The pressure of reactor and saturator is maintained at 9.5 psig. The reaction products are absorbed in chilled to 10° C. dichloromethane and the solution of reaction products in dichloromethane us analyzed by gas chromatography. The line between the saturator and the reactor as well as the line between the reactor and absorber are heat traced to prevent condensation of 3-methyloxetan-2-one to methacrylic acid. The reaction is conducted at the reactor temperature of 210° C. At these conditions, 3-methyloxetan-2-one conversion of greater than 99.9% is observed with selectivity of methacrylic acid product of greater than 98% (WHSV at these conditions is 0.45 h-1).

Example 23: Conversion of Acrylic Acid to Acrylonitrile

The ammoxidation reaction generally refers to the one-step formation of nitrile compounds in a single step by the oxidation of simple olefins, aromatics, heteroaromatics or an acid in the presence of oxygen and ammonia in the gas phase. Supported molybdenum oxide catalysts are known and widely investigated as they represent an important group of catalysts for the heterogeneous oxidation and ammoxidation of hydrocarbons.

Catalyst Preparation

The MoO3/ZrO2 and MoO3/γ-Al2O3 catalysts are prepared by impregnation of γAl2O3 or ZrO2 with a 2 M oxalic solution of ammonium heptamolybdate. The mixture is left in an open vessel with stirring at 60° C. for 24 h to evaporate the excess water. The precursor is dried at 100° C. for 12 h and calcined at 500° C. for 6 h before use.

A series of MoO3/ZrO2/γ-Al2O3 catalysts with MoO3 loadings in the range of 6.6-25.0 wt. % are prepared by wet impregnation method. To impregnate MoO3, the calculated amount of ammonium heptamolybdate is dissolved in 30-40 ml doubly distilled water and reflux at 85-90° C. for 5 h. Then, a few drops of dilute NH4OH are added to make the solution clear and keep the pH constant (pH=8). After impregnation, the reaction mixture is added to a 50 ml Pyrex flask. The mixture is irradiated in the water bath of the ultrasonic at 20 kHz for 1 h within the temperature range of 25-30° C. Then the catalysts are dried at 85-90° C. for about 4 h and calcined at 500° C. for 6 h before use.

Ammoxidation of Acrylic Acid

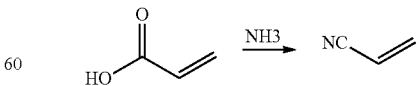

A stainless steel cylindrical micro reactor (i.d. 4.8 cm; a reactor length of 8.55 cm; volume 150 cm3), is charged with acrylic acid (3 ml), 20 mg catalyst and a magnetic stirring bar. The autoclave is purged and filled with NH3 until the pressure reached 0.75 MPa. Then 02 is introduced until the total pressure reached to 1.25 MPa. The reaction mixture is stirred at a controlled temperature (400° C. for 2 h). After the reaction, the mixture is filtered. The filtrate is analyzed by GC-MS and GC using acrylonitrile as an internal standard. For recycling tests, the catalyst is filtered after the reaction, washed with acetone three times and then with doubly distilled water several times. Then, it is dried at 110° C., calcined at 400° C. for 4 h, and then used for the next run.

Example 24: Esterification of Acrylic Acid

Example 24 is disclosed in granted U.S. Pat. No. 3,458,561, herein incorporated by reference.

In a heated reactor provided with a thermometer, stirring, feed, and recovery means, and where reactor's reboiler contains 600 grams of p-toluene sulfonic acid and 400 grams acrylic acid, a mixture of 580 grams of acrylic acid and 390 grams ethanol is introduced. The reboiler temperature is 125° C. A pressure of 200 mmHg exists in the apparatus. The formed acrylic acid ethyl ester together with the water of reaction and slight amount of water originating from the industrial acrylic acid is removed through a column and an attached pressure-equalizing cooler. A slight excess of about 0.05 mole per mole of acrylic acid of alcohol is found at the head of the column. During 35 hours, an hourly average of 960 grams of distillate are recovered. The distillate forms layers. The upper water-containing ester layer and the lower ester-containing water layer are divided and worked up separately. According to the described procedure, on the average about 768 grams of acrylic acid ethyl ester are isolated per hour. On the basis of the introduced acrylic acid, this amount corresponds to a yield of 95.2%.

Example 25

In a semi-works installation, which in its construction basically corresponds to the apparatus described in Example 24, into a reboiler mixture of 160 kilograms acrylic acid and 40 kilograms 100.3% sulfuric acid, on an hourly basis, 200 kilograms of acrylic acid and 150 kilograms of ethanol are introduced continuously. During an operation of 180 days, 1166 metric tons of raw ester are recovered. On an average hourly basis, it corresponds to 270 kilograms of acrylic acid ethyl ester being produced. On the basis of the acrylic acid introduced hourly, it corresponds to a yield of 97%.

Although the reboiler contents turn to a brownish-black color within a short time, nevertheless, it is still useful for the esterification of the additional acrylic acid.

Example 26: Ammoxidation of Acrylic Acid Ethyl Ester

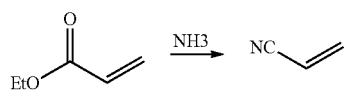

A stainless steel cylindrical micro reactor (i.d. 4.8 cm; a reactor length of 8.55 cm; volume 150 cm3), is charged with acrylic acid ethyl ester (3 ml), 20 mg catalyst and a magnetic stirring bar. The autoclave is purged and filled with NH3 until the pressure reached 0.75 MPa. Then O2 is introduced until the total pressure reached to 1.25 MPa. The reaction mixture is stirred at a controlled temperature (400° C. for 2 h). After the reaction, the mixture is filtered. The filtrate is analyzed by GC-MS and GC using acrylonitrile as an internal standard. For recycling tests, the catalyst is filtered after the reaction, wash with acetone three times and then with doubly distilled water several times. Then, it is dried at 110° C., calcined at 400° C. for 4 h, and then used for the next run.

The embodiments described herein are not intended to be limited to the aspects shown, but are to be accorded the widest scope consistent with the principles and features disclosed herein.

What is claimed is:

1. A process for producing an acrylonitrile product, comprising:
   introducing an epoxide reagent and a carbon monoxide reagent to at least one reaction vessel through at least one feed stream inlet;
   contacting the epoxide reagent and the carbon monoxide reagent with a carbonylation catalyst in the at least one reaction vessel to produce a beta-lactone intermediate;
   converting the beta-lactone intermediate to an organic acid intermediate; and
   reacting the organic acid intermediate with an ammonia reagent under ammoxidation conditions in the at least one reaction vessel to produce the acrylonitrile product.

2. The process of claim 1, wherein the converting of the beta-lactone intermediate to the organic acid intermediate comprises:
   polymerizing the beta-lactone intermediate with a polymerization initiator in the at least one reaction vessel to produce a polylactone product; and
   heating the polylactone product under thermolysis conditions in the at least one reaction vessel to produce the organic acid intermediate.

3. The process of claim 1, wherein the carbonylation catalyst comprises one or more metal carbonyl-Lewis acid catalysts.

4. The process of claim 1, wherein the carbonylation catalyst is introduced to the at least one reaction vessel under a carbon monoxide blanket.

5. The process of claim 1, wherein the carbonylation catalyst comprises a neutral metal carbonyl compound.

6. The process of claim 2, wherein the polymerization initiator has the general formula of M"X, where M" is cationic and X is anionic.

7. The process of claim 2, wherein the polymerization initiator comprises a carboxylate salt.

8. The process of claim 2, wherein the polylactone product undergoes thermolysis continuously.

9. The process of claim 1, wherein the converting of the beta-lactone intermediate to the organic acid intermediate comprises:
   contacting the beta-lactone intermediate with a heterogenous catalyst to directly produce the organic acid intermediate.

* * * * *